US 10,646,384 B2

(12) United States Patent
Moriya et al.

(10) Patent No.: US 10,646,384 B2
(45) Date of Patent: May 12, 2020

(54) ABSORBENT ARTICLE AND WEARABLE ARTICLE INCLUDING ABSORBENT ARTICLE

(71) Applicant: UNICHARM CORPORATION, Ehime (JP)

(72) Inventors: Ayako Moriya, Kanonji (JP); Hideyuki Ishikawa, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 717 days.

(21) Appl. No.: 15/323,042

(22) PCT Filed: Dec. 19, 2014

(86) PCT No.: PCT/JP2014/083775
§ 371 (c)(1),
(2) Date: Dec. 29, 2016

(87) PCT Pub. No.: WO2016/002105
PCT Pub. Date: Jan. 7, 2016

(65) Prior Publication Data
US 2017/0135872 A1     May 18, 2017

(30) Foreign Application Priority Data

Jun. 30, 2014 (JP) ................................ 2014-135468
Nov. 14, 2014 (JP) ................................ 2014-232183

(51) Int. Cl.
*A61F 13/15*     (2006.01)
*A61F 13/538*     (2006.01)
(Continued)

(52) U.S. Cl.
CPC ...... *A61F 13/538* (2013.01); *A61F 13/49001* (2013.01); *A61F 13/511* (2013.01);
(Continued)

(58) Field of Classification Search
CPC .............. A61F 13/538; A61F 13/49001; A61F 13/5121; A61F 13/539; A61F 2013/5395
See application file for complete search history.

(56) References Cited

U.S. PATENT DOCUMENTS 5,037,416 A * 8/1991 Allen ................ A61F 13/49009
604/385.22
2002/0068150 A1   6/2002   Taneichi et al.
(Continued)

FOREIGN PATENT DOCUMENTS

JP     2002-187228 A     7/2002
JP     2003-247155 A     9/2003
(Continued)

OTHER PUBLICATIONS

International Search Report in PCT/2014/083775, dated Mar. 24, 2015.

*Primary Examiner* — Jacqueline F Stephens
(74) *Attorney, Agent, or Firm* — Hauptman Ham, LLP

(57) ABSTRACT

As absorbent article for absorbing urine includes a topsheet which is a nonwoven fabric that has a skin-side surface having projections formed thereon. The content by percentage of fibers oriented in the thickness direction in each projection of the nonwoven fabric is greater than the content by percentage of fibers oriented in the thickness direction in sections of the nonwoven fabric other than the projections. The thickness of the nonwoven fabric when wet is greater than or equal to 85% the thickness of the nonwoven fabric when dry. The nonwoven fabric includes a first fiber layer and a second fiber layer. The first fiber layer is constituted by durable hydrophilic fibers, and the second fiber layer is constituted by durable hydrophilic fibers and non-durable hydrophilic fibers.

10 Claims, 13 Drawing Sheets

(51) Int. Cl.
  *A61F 13/511* (2006.01)
  *A61F 13/513* (2006.01)
  *A61F 13/536* (2006.01)
  *A61F 13/49* (2006.01)
  *A61F 13/512* (2006.01)
  *A61F 13/539* (2006.01)

(52) U.S. Cl.
  CPC ........ *A61F 13/513* (2013.01); *A61F 13/5116* (2013.01); *A61F 13/5121* (2013.01); *A61F 13/51104* (2013.01); *A61F 13/51108* (2013.01); *A61F 13/536* (2013.01); *A61F 13/539* (2013.01); *A61F 2013/51178* (2013.01); *A61F 2013/5395* (2013.01)

(56) References Cited

U.S. PATENT DOCUMENTS

| | | |
|---|---|---|
| 2003/0162460 A1 | 8/2003 | Saka et al. |
| 2004/0140047 A1 | 7/2004 | Sato et al. |
| 2006/0069371 A1 | 3/2006 | Ohashi et al. |
| 2007/0298213 A1 | 12/2007 | Noda et al. |
| 2007/0298214 A1 | 12/2007 | Noda et al. |
| 2007/0298220 A1 | 12/2007 | Noda et al. |
| 2007/0298667 A1 | 12/2007 | Noda et al. |
| 2007/0298671 A1 | 12/2007 | Noda et al. |
| 2007/0299416 A1 | 12/2007 | Noda et al. |
| 2008/0044622 A1 | 2/2008 | Noda et al. |
| 2008/0044628 A1 | 2/2008 | Noda et al. |
| 2008/0045915 A1 | 2/2008 | Noda et al. |
| 2008/0085399 A1 | 4/2008 | Noda et al. |
| 2009/0282660 A1 | 11/2009 | Noda et al. |
| 2010/0191207 A1 | 7/2010 | Oba et al. |
| 2010/0249740 A1 | 9/2010 | Miyamoto et al. |
| 2012/0220972 A1 | 8/2012 | Kawamura et al. |
| 2012/0321839 A1 | 12/2012 | Uematsu et al. |
| 2014/0039434 A1* | 2/2014 | Xu .................. A61F 13/538 604/368 |

FOREIGN PATENT DOCUMENTS

| | | |
|---|---|---|
| JP | 2004-174234 A | 6/2004 |
| JP | 2005-324010 A | 11/2005 |
| JP | 2005-350836 A | 12/2005 |
| JP | 2006-95156 A | 4/2006 |
| JP | 2007-44124 A | 2/2007 |
| JP | 2007-177340 A | 7/2007 |
| JP | 2008-23326 A | 2/2008 |
| JP | 2008-25079 A | 2/2008 |
| JP | 2009-30218 A | 2/2009 |
| JP | 2009-160035 A | 7/2009 |
| JP | 2009-201964 A | 9/2009 |
| JP | 2010-168715 A | 8/2010 |
| JP | 2011-104021 A | 6/2011 |
| JP | 2011-168927 A | 9/2011 |
| JP | 2012-5701 A | 1/2012 |
| JP | 2013-119012 A | 6/2013 |
| JP | 2014-18280 A | 2/2014 |

* cited by examiner

ABSORBENT ARTICLE AND WEARABLE ARTICLE INCLUDING ABSORBENT ARTICLE

RELATED APPLICATIONS

The present application is a National Phase of International Application Number PCT/JP2014/083775, filed Dec. 19, 2014, which claims priority to Japanese Applications Number 2014-135468, filed Jun. 30, 2014 and Number 2014-232183, filed Nov. 14, 2014.

TECHNICAL FIELD

The present invention relates to an absorbent article and to a wearable article provided with an absorbent article.

BACKGROUND ART

PTL 1 describes an absorbent article, and specifically an absorbent pad, having an absorbent body with rows of perforated holes disposed in the section that contacts with the genitals of the wearer. With the absorbent article described in PTL 1 it is possible to improve the fitting property of the absorbent article for the genital area of the wearer. Moreover, because the section that contacts with the genitals of the wearer is resistant to becoming moist, it is possible to prevent discomfort for the wearer.

Also, in PTLs 2 to 13 there are disclosed nonwoven fabrics having projections formed on the surface, and the use of the nonwoven fabrics as top sheets for absorbent articles. In the nonwoven fabrics described in PTLs 2 to 13, it is possible to improve the liquid permeability and feel on the skin of the nonwoven fabric by the projections formed on the surface.

CITATION LIST

Patent Literature

PTL 1 Japanese Unexamined Patent Publication No. 2006-95156
PTL 2 Japanese Unexamined Patent Publication No. 2009-30218
PTL 3 Japanese Unexamined Patent Publication No. 2008-23326
PTL 4 Japanese Unexamined Patent Publication No. 2008-25079
PTL 5 Japanese Unexamined Patent Publication No. 2004-174234
PTL 6 Japanese Unexamined Patent Publication No. 2009-160035
PTL 7 Japanese Unexamined Patent Publication No. 2009-201964
PTL 8 Japanese Unexamined Patent Publication No. 2012-5701
PTL 9 Japanese Unexamined Patent Publication No. 2002-187228
PTL 10 Japanese Unexamined Patent Publication No. 2003-247155
PTL 11 Japanese Unexamined Patent Publication No. 2007-177340
PTL 12 Japanese Unexamined Patent Publication No. 2005-350836
PTL 13 Japanese Unexamined Patent Publication No. 2010-168715

SUMMARY OF INVENTION

Technical Problem

When the absorbent pads mentioned above have been used by bedridden elderly, for example, the absorption property for urine has been inferior and urine has sometimes leaked from the absorbent pad.

The present inventors have confirmed that the urine of bedridden elderly contains large amounts of solid components compared to the urine of adults in general, and we have found that such solid components clog the top sheet of the absorbent pad and inhibit absorption property of urine.

It is an object of the present invention to provide an absorbent article with an excellent absorption property for urine containing solid components and resistance to leakage of urine containing solid components, as well as a wearable article provided with the absorbent article.

Solution to Problem

In order to solve the problems described above, the present invention provides an absorbent article for absorbing urine containing a solid component, wherein the absorbent article comprises a liquid-permeable top sheet, a liquid-impermeable back sheet and a liquid-absorbing absorbent body disposed between the top sheet and the back sheet, and has a lengthwise direction, a widthwise direction and a thickness direction that are mutually orthogonal, the top sheet is a nonwoven fabric with a skin side surface in which a projection is formed, a content of fibers oriented in the thickness direction at the projection of the nonwoven fabric is greater than a content of fibers oriented in the thickness direction at a section other than the projection of the nonwoven fabric, a wet thickness of the nonwoven fabric is at least 85% of a dry thickness of the nonwoven fabric, the nonwoven fabric has a first fiber layer with a skin side surface and a second fiber layer located more toward the absorbent body side than the first fiber layer, the first fiber layer is composed of fibers with durable hydrophilicity and the second fiber layer is composed of fibers with durable hydrophilicity and fibers with non-durable hydrophilicity.

The present invention further provides a wearable article comprising an exterior body provided with a liquid-permeable top sheet with a fitting side in which the absorbent article is fitted, and a liquid-impermeable back sheet, and having an abdomen side section, a crotch section and a back side section, and an absorbent article of the invention fitted in a detachable manner on the fitting side.

Advantageous Effects of Invention

The absorbent article of the invention, and the wearable article provided with the absorbent article, have an excellent absorption property for urine containing solid components and resistance to leakage of urine containing solid components.

DESCRIPTION OF EMBODIMENTS

Figure 1:
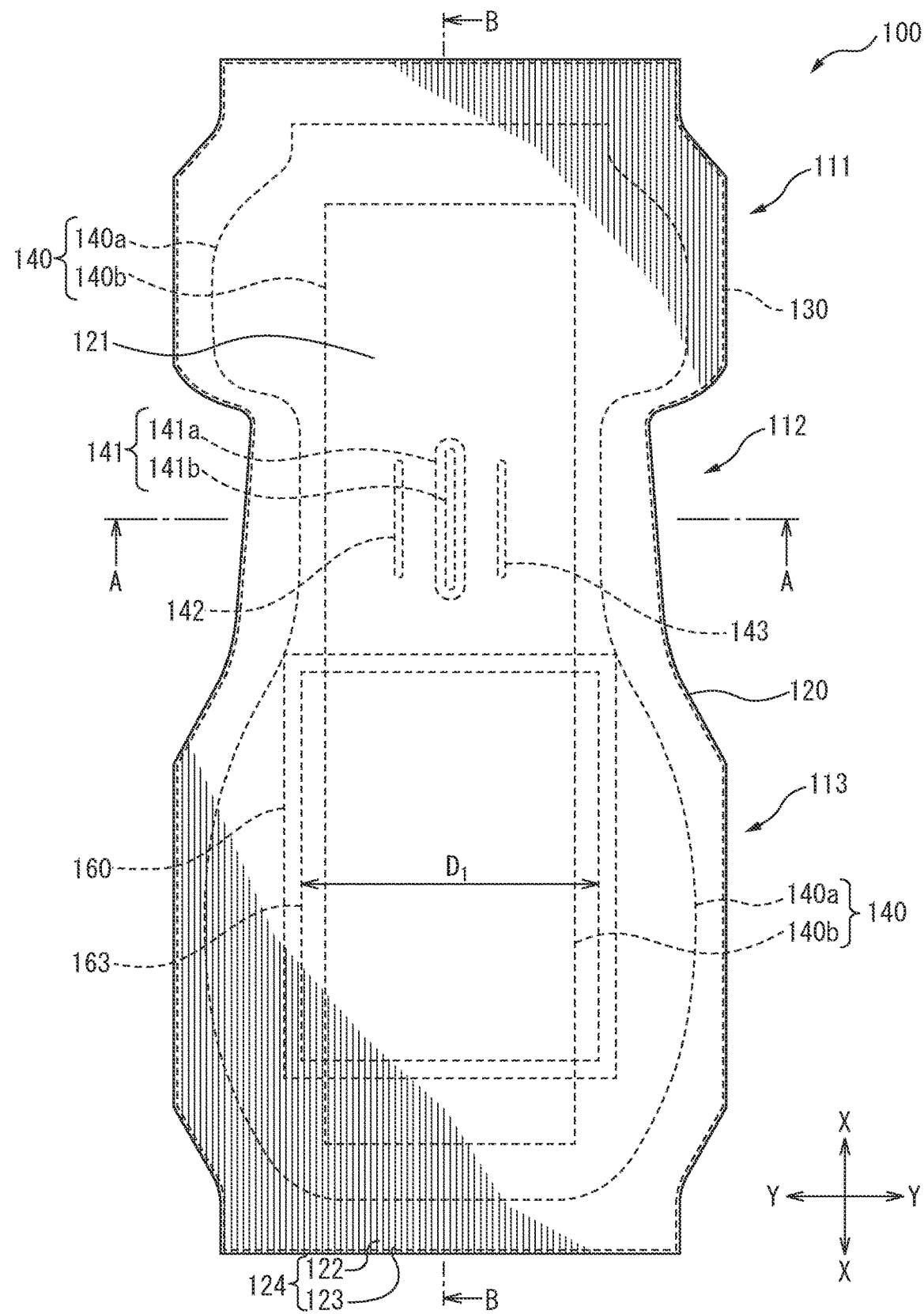
FIG. 1 is a plan view of a urine-absorbing pad according to an embodiment of the invention.

Throughout the present specification, among both long sides, the proximal side to an imaginary center line extending in the widthwise direction through the center of the absorbent article will be referred to as the "inner side in the lengthwise direction", and the distal side will be referred to as the "outer side in the lengthwise direction". Also, among both sides in the widthwise direction, the proximal side to an imaginary center line extending in the lengthwise direction through the center of the absorbent article will be referred to as the "inner side in the widthwise direction", and the distal side will be referred to as the "outer side in the widthwise direction". In addition, among both sides in the thickness direction, the side in the thickness direction located on the skin side of the wearer will be referred to as the "skin side", and the other side in the thickness direction located on the clothing side of the wearer will be referred to as the "clothing side".

Aspects included within the concept of the absorbent article for absorption of urine containing solid components according to the invention (hereunder, "absorbent article for absorption of urine containing solid components" will also be referred to simply as "absorbent article") will now be described.

An absorbent article according to one aspect of the invention (hereunder, "aspect 1A") is an absorbent article for absorbing urine containing a solid component, wherein the absorbent article comprises a liquid-permeable top sheet, a liquid-impermeable back sheet and a liquid-absorbing absorbent body disposed between the top sheet and the back sheet, and has a lengthwise direction, a widthwise direction and a thickness direction that are mutually orthogonal, the top sheet is a nonwoven fabric with a skin side surface in which a projection is formed, a content of fibers oriented in the thickness direction at the projection of the nonwoven fabric is greater than the content of fibers oriented in the thickness direction at a section other than the projection of the nonwoven fabric, a wet thickness of the nonwoven fabric is at least 85% of a dry thickness of the nonwoven fabric, the nonwoven fabric has a first fiber layer with a skin side surface and a second fiber layer located more toward the absorbent body side than the first fiber layer, the first fiber layer is composed of fibers with durable hydrophilicity and the second fiber layer is composed of fibers with durable hydrophilicity and fibers with non-durable hydrophilicity.

The absorbent article of aspect 1A can exhibit the following function and effect. Because the content of fibers oriented in the thickness direction in the projections of the nonwoven fabric is greater than the content of fibers oriented in the thickness direction in the other sections, and the wet thickness of the nonwoven fabric is at least 85% of the dry thickness of the nonwoven fabric, when the top sheet is in a moist state due to liquids supplied to the absorbent article, the shapes of the projections formed in the top sheet are maintained and the voids in the top sheet are easily preserved.

Investigation by the present inventors has indicated that urine of the elderly, and especially the bedridden elderly, contains more solid components such as magnesium ammonium phosphate stones, calcium oxalate crystals, epithelial cells and hyaline casts, compared to the urine of adults in general.

Throughout the present specification, such solid components in urine may be referred to simply as "solid components".

In the absorbent article of aspect 1A, the nonwoven fabric has a first fiber layer with a skin side surface and a second fiber layer located further on the absorbent body side than the first fiber layer, the first fiber layer being composed of fibers with durable hydrophilicity and the second fiber layer being composed of fibers with durable hydrophilicity and fibers with non-durable hydrophilicity, and therefore urine that has been supplied to the absorbent article passes through the top sheet and rapidly migrates to the absorbent body, such that the urine supplied to the absorbent article does not easily leak. In addition, because the solid components do not easily block the voids of the top sheet and the surface of the absorbent body upon absorption of urine, the urine supplied to the absorbent article does not easily leak even with repeated absorption of urine.

This aspect is advantageous as an absorbent article (for example, a urine-absorbing pad) for absorption of elderly (especially bedridden elderly) urine, since the absorbent article of aspect 1A easily maintains the bulk of the projections, and the voids. The term "elderly" generally means a person of 65 years or older.

The absorbent article of aspect 1A has an excellent absorption property for urine in general that contains solid components, such as that resulting from diseases or the like, without being limited to the elderly so long as it is urine containing solid components.

Such diseases include renal calculus, gout, acute hepatitis and the like in which crystalline components are increased, cystitis, nephritis and the like in which epithelial cells are increased, and pyelonephritis, diabetic nephropathy and the like in which columnar cells are increased.

The absorbent article of aspect 1A can absorb urine, and especially urine containing solid components, without leakage up to several times, preferably 3 or more times, more preferably 4 or more times and even more preferably 5 or more times. The absorbent article of aspect 1A can absorb urine, and especially urine containing solid components, without leakage up to an amount of preferably 400 mL or more, more preferably 500 mL or more and even more preferably 600 mL or more.

For example, most bedridden elderly urinate about 3 or more times per night for a total of 400 mL or more, and if it is possible to absorb at least 3 times, or 400 mL of urine, without leakage, then this can reduce the amount of exchange of the absorbent article at nighttime, and minimize nighttime sleep disturbances for the elderly. In addition, it can reduce the time that caregivers must devote to exchanging absorbent articles during nighttime, alleviating the burden of nursing, and specifically excretion care.

According to a preferred aspect of the absorbent article of aspect 1A (hereunder, "aspect 2A"), the dry thickness of the nonwoven fabric is 0.6 to 1.6 mm. This increases the total amount of voids in the top sheet (nonwoven fabric), so that blocking of the top sheet by solid components is inhibited and leakage of urine from the absorbent article is inhibited, even when urine has been absorbed several times.

According to a preferred aspect of the absorbent article of aspect 1A or aspect 2A (hereunder, "aspect 3A"), a basis weight of the nonwoven fabric is 18 to 40 g/m$^2$. This will allow the top sheet (nonwoven fabric) to have a fixed fiber density both when dry and when wet, thereby facilitating preservation of the voids through which solid components pass.

According to a preferred aspect of the absorbent article according to any of aspect 1A to aspect 3A (hereunder, "aspect 4A"), the nonwoven fabric is produced by spraying gas onto a web containing thermoplastic resin fibers to form a web having an irregular structure, and then heating the web having the irregular structure to cause heat fusion of crossing sections of the thermoplastic resin fibers therein. This will allow the top sheet (nonwoven fabric) to preserve the voids through which solid components pass, not only when dry but also when wet.

According to a preferred aspect of the absorbent article according to any of aspect 1A to aspect 4A (hereunder, "aspect 5A"), the absorbent body has a through-hole running through the absorbent body in the thickness direction or a recess that opens to the top sheet side, the through-hole or recess extends in the lengthwise direction, through a center in the widthwise direction of the absorbent body. Due to the force on the inner side in the widthwise direction, that is applied when the absorbent article is worn, the skin side surface of the top sheet readily deforms outward toward the clothing side (back sheet side) with the portions other than the projections (for example, the recess) as the bending origins, while the absorbent body readily deforms outward toward the skin side (top sheet side). Thus, when the absorbent article is worn, the top sheet enters into the through-hole or the recess of the absorbent body. Consequently, even when the top sheet is pressed when the absorbent article is being worn, the portions of the top sheet that have entered into the through-hole or recess of the absorbent body are resistant to the pressing force, and the shapes of the projections are easily maintained at those portions.

According to a preferred aspect of the absorbent article of aspect 5A (hereunder, "aspect 6A"), the absorbent body has a compressed section formed by compressing the absorbent body in the thickness direction, further on an outer side in the widthwise direction than the through-hole or recess. Force directed to the inner side in the widthwise direction, which is applied when the absorbent article is worn, causes the absorbent body to easily deform outward to the skin side, with the compressed sections as bending origins. Thus, when the absorbent article is worn, the top sheet enters into the through-hole or the recess of the absorbent body. In addition, since the shape of the through-hole or recess of the absorbent body can be easily preserved by the compressed sections, the space of the through-hole or recess in which the top sheet enters is also easily maintained.

According to a preferred aspect of the absorbent article of aspect 5A or 6A (hereunder, "aspect 7A"), a fluid-absorbing sheet is disposed between the top sheet and the absorbent body, the fluid-absorbing sheet having two liquid-permeable sheets and an absorbent polymer layer disposed between the two liquid-permeable sheets, while the fluid-absorbing sheet is disposed so that the fluid-absorbing sheet does not overlap the through-hole or recess in the thickness direction. As a result, when urine is supplied to the absorbent article, the absorbent polymer layer absorbs the urine and swells, increasing the thickness of the absorbent polymer layer. Since the polymer layer whose thickness has increased functions as a pressure buffering layer, the through-hole or recess that does not overlap the absorbent polymer layer in the thickness direction of the top sheet is protected from pressure, while the portions of the top sheet that overlap the through-hole or recess in the thickness direction are resistant to pressing force, and the shapes of the projections and the voids in the top sheet at those portions can be easily maintained. As a result, the top sheet is resistant to blocking by solid components in urine, and leakage of urine from the absorbent article is minimized.

According to a preferred aspect of the absorbent article of any of aspect 1A to aspect 7A (hereunder, "aspect 8A"), the projection is a plurality of ridges extending in the lengthwise direction, and furrows are formed between the plurality of ridges, extending in the lengthwise direction. Thus, urine that has reached the top sheet spreads out throughout the furrows, increasing the area of the entrance for urine in the top sheet, thereby further preventing leakage of urine.

Aspects encompassed by the wearable article of the invention will now be described.

A wearable article according to one aspect of the invention (hereunder, "aspect 1B") is a wearable article comprising an exterior body provided with a liquid-permeable top sheet with a fitting side in which an absorbent article is fitted, and a liquid-impermeable back sheet, and having an abdomen side section, a crotch section and a back side section, and an absorbent article according to any one of aspect 1A to aspect 8A fitted in a detachable manner on the fitting side.

The wearable article of aspect 1B can exhibit the same function and effect as the absorbent article according to aspect 1A to aspect 8A, depending on the aspect of the absorbent article that is fitted.

A aspect of the nonwoven fabric of the invention will now be described.

A nonwoven fabric according to one aspect of the invention (hereunder, "aspect 1C") is a nonwoven fabric for a top sheet of an absorbent article for absorbing urine containing a solid component, and the absorbent article comprises a liquid-permeable top sheet, a liquid-impermeable back sheet and a liquid-absorbing absorbent body disposed between the top sheet and the back sheet, and has a lengthwise direction, a widthwise direction and a thickness direction that are mutually orthogonal, wherein the nonwoven fabric has a skin side surface in which a projection is formed, a content of fibers oriented in the thickness direction at the projection of the nonwoven fabric is greater than a content of fibers oriented in the thickness direction at a section other than the projection of the nonwoven fabric, a wet thickness of the nonwoven fabric is at least 85% of a dry thickness of the nonwoven fabric, and the nonwoven fabric has a first fiber layer with a skin side surface and a second fiber layer located more toward the absorbent body side than the first fiber layer, the first fiber layer is composed of fibers with durable hydrophilicity and the second fiber layer is composed of fibers with durable hydrophilicity and fibers with non-durable hydrophilicity.

The nonwoven fabric of aspect 1C can exhibit the same function and effect as the absorbent article according to aspect 1A to aspect 8A, depending on the aspect of the absorbent article that is fitted.

There are no particular restrictions on the type and usage of the absorbent article of the invention. For example, absorbent articles include sanitary products such as urine-absorbing pads, disposable diapers, sanitary napkins and panty liners, which may be for humans or animals other than humans, such as pets. There are no particular restrictions on the fluid to be absorbed by the absorbent article of the invention, and for example, it may be liquid excreta (for example, urine, watery stool or menstrual blood) of the wearer.

Figure 2:
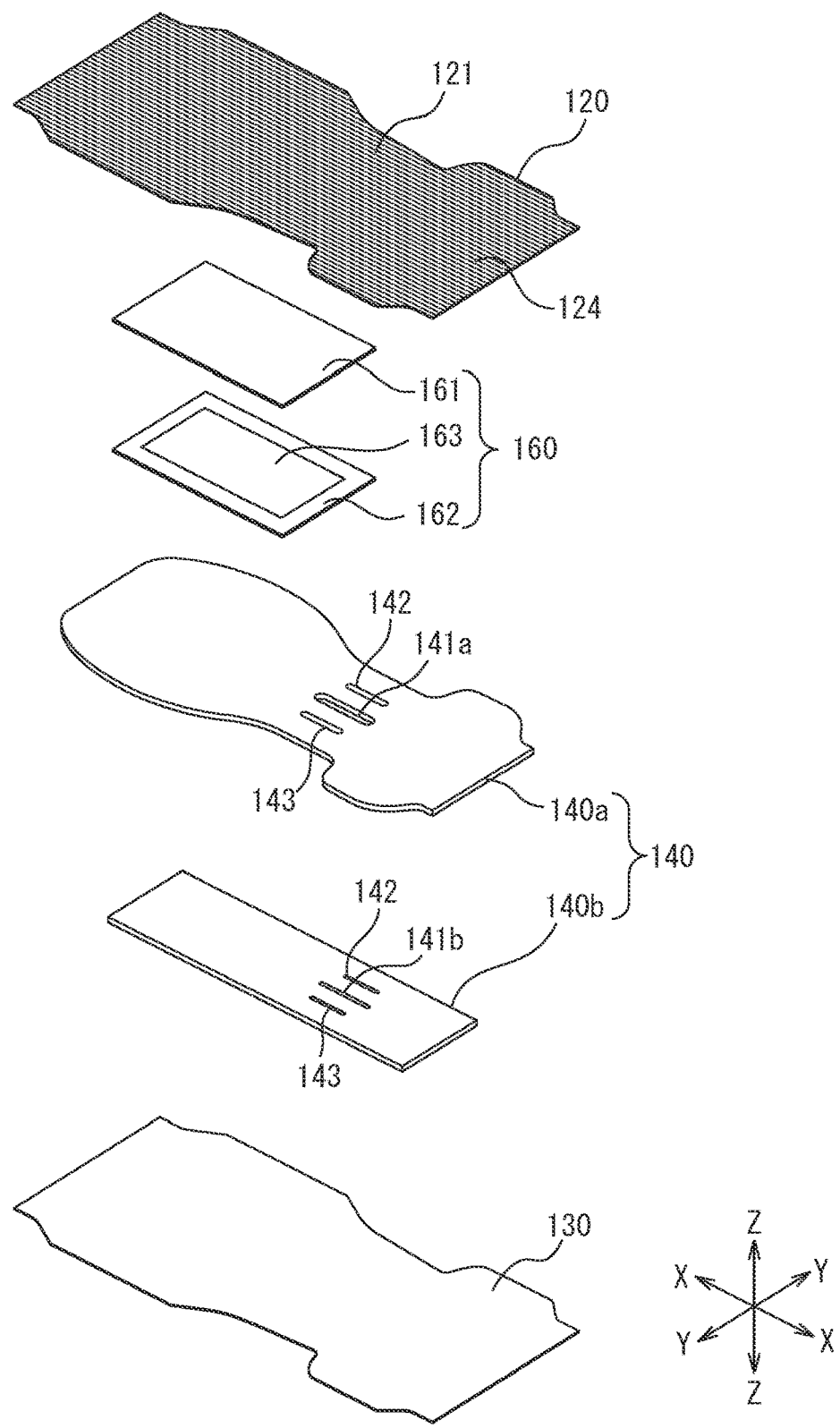
FIG. 2 is an exploded perspective view of the urine-absorbing pad shown in FIG. 1.
Figure 3:
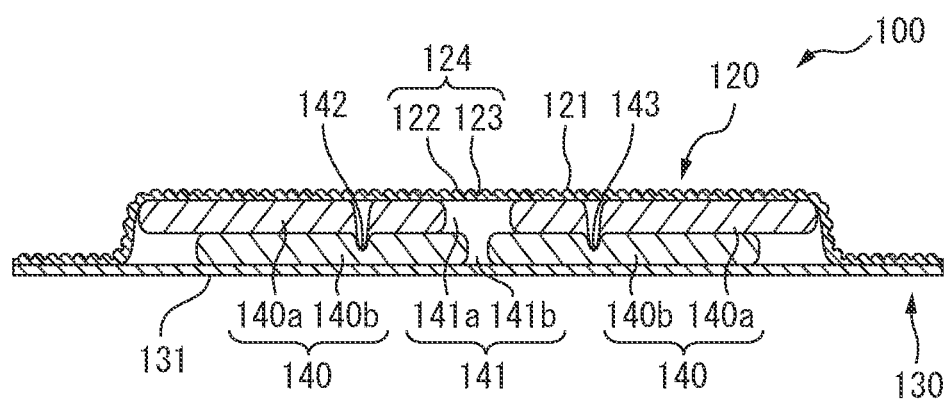
FIG. 3 is an end view along line A-A of FIG. 1.
Figure 3:
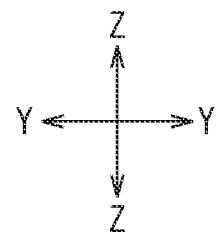
Figure 4A:
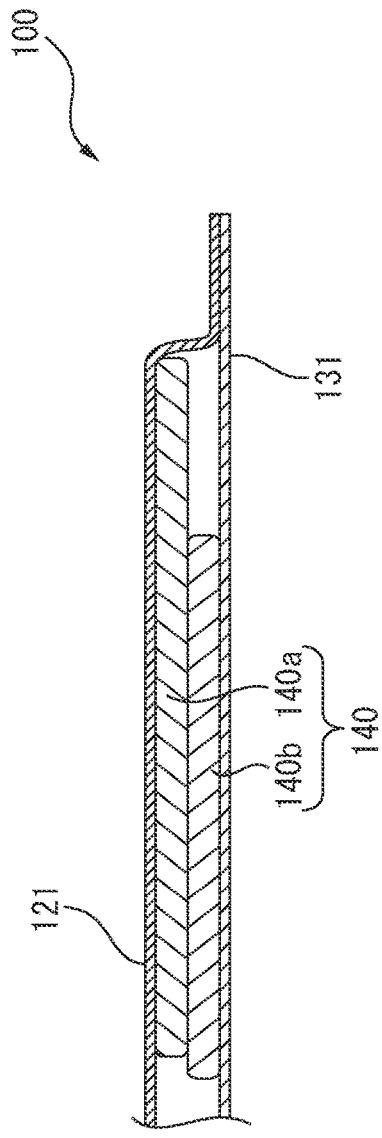
FIG. 4(A) is an end view along line B-B of FIG. 1 (the portion on the abdomen section side)
Figure 4B:
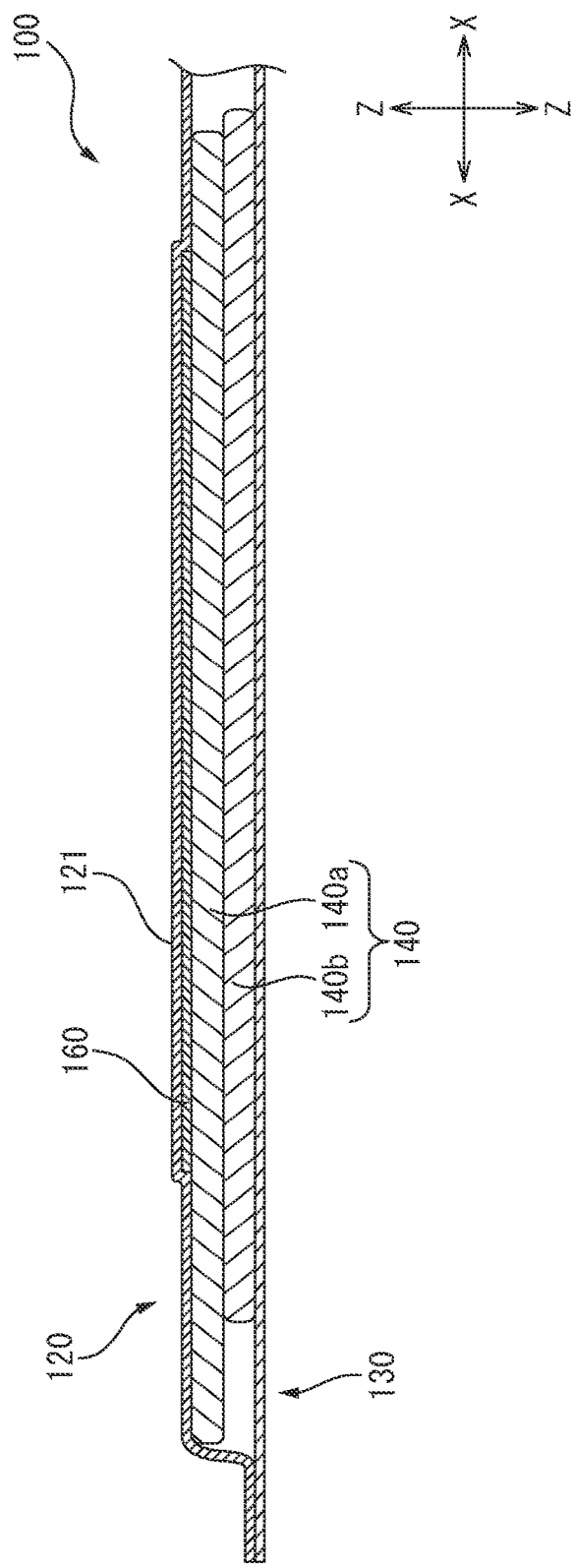
FIG. 4(B) is an end view along line B-B of FIG. 1 (the portion on the back section side).
Figure 5:
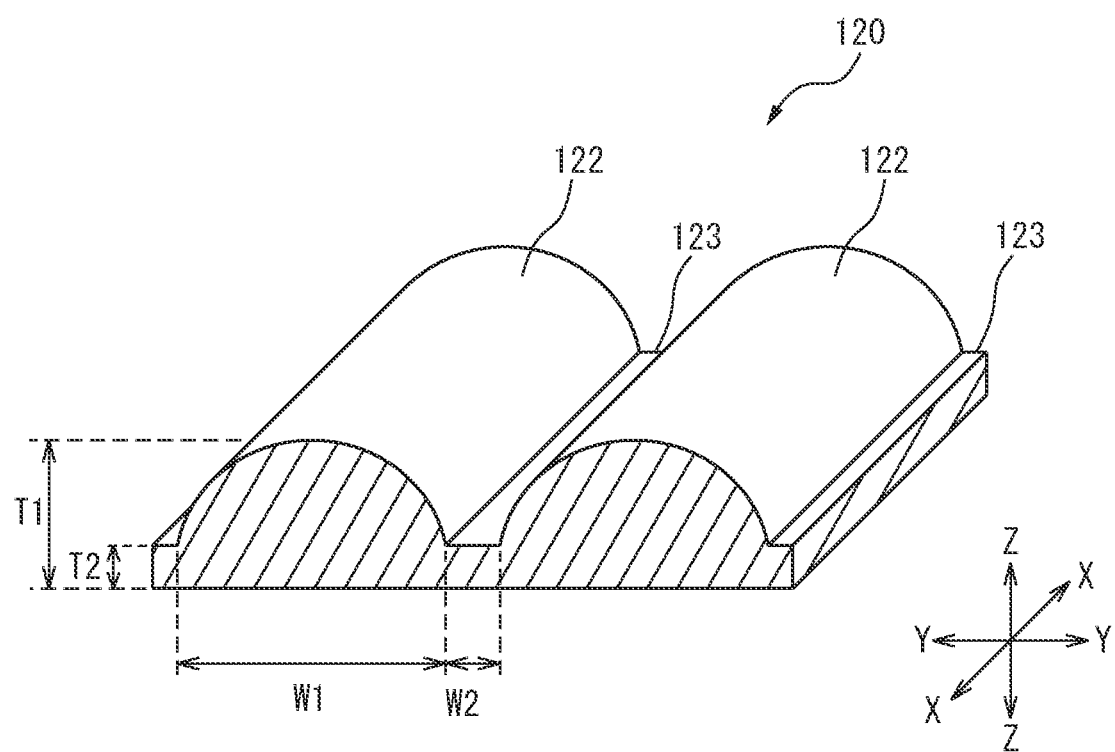
FIG. 5 is a partial magnified perspective view of the top sheet in the urine-absorbing pad shown in FIG. 1.

A urine-absorbing pad 100 will now be described as an embodiment of the absorbent article of the invention, with reference to FIG. 1 to FIG. 5. FIG. 1 is a plan view of a urine-absorbing pad 100, FIG. 2 is an exploded perspective view of the urine-absorbing pad 100, FIG. 3 is an end view along line A-A of FIG. 1, FIG. 4 is an end view along line B-B of FIG. 1 (A being the portion on the abdomen side section side and B being the portion on the back side section side), and FIG. 5 is a partial magnified perspective view of the top sheet 120.

In its spread-out state, the urine-absorbing pad 100 has a lengthwise direction X, a widthwise direction Y and a thickness direction Z that are mutually orthogonal.

The urine-absorbing pad 100 comprises a liquid-permeable top sheet 120 having a skin side surface 121, a liquid-impermeable back sheet 130 having a clothing side surface 131, and a liquid-absorbing absorbent body 140 disposed between the top sheet 120 and the back sheet 130.

The urine-absorbing pad 100 has an abdomen side section 111, a crotch section 112 and a back side section 113, aligned in the lengthwise direction X. When the urine-absorbing pad 100 is worn, the abdomen side section 111 touches the abdominal region of the wearer, the crotch section 112 touches the crotch region of the wearer, and the back side section 113 touches the gluteal region and/or the back region of the wearer. The length of the urine-absorbing pad 100 will usually be 350 to 880 mm, and the width will usually be 160 to 460 mm.

The urine-absorbing pad 100 is worn in such a manner that the skin side surface 121 of the top sheet 120 is located on the skin side of the wearer and the clothing side surface 131 of the back sheet 130 is located on the clothing side of the wearer. The urine-absorbing pad 100 is preferably worn in a manner fitted in the exterior body 200, described hereunder. The shape of the urine-absorbing pad 100 as viewed flat is a gourd-shape narrowed at approximately the center in the lengthwise direction X, and therefore the narrowed section of the urine-absorbing pad 100 easily fits into the crotch of the wearer. Urine that has been discharged by the wearer penetrates into the absorbent body 140 through the top sheet 120, and is absorbed and held in the absorbent body 140. Leakage of urine that has been absorbed and held by the absorbent body 140 is prevented by the back sheet 130.

The liquid-permeable sheet used for the top sheet 120 is a nonwoven fabric. Examples of nonwoven fabrics include air-through nonwoven fabrics, spunbond nonwoven fabrics, point bond nonwoven fabrics, spunlace nonwoven fabrics, needle punching nonwoven fabrics and meltblown nonwoven fabrics, as well as combinations thereof (such as spunbond/melt blown/spunbond (SMS) nonwoven fabrics and the like), but air-through nonwoven fabrics are preferred. The basis weight of the nonwoven fabric used as the top sheet 120 is appropriately adjusted in consideration of the liquid permeability, feel on the skin and the like.

Ridges 122 (an example of projections) are formed on the skin side surface 121 of the top sheet 120. The ridges 122 extend in the lengthwise direction X and are aligned at prescribed spacings in the widthwise direction Y, with one furrow 123 being formed between every two adjacent ridges 122. In other words, on the skin side surface 121 there is formed a ridge-furrow structure 124 comprising a plurality of ridges 122 extending in the lengthwise direction X, and a plurality of furrows 123 extending in the lengthwise direction X. In FIG. 1 and FIG. 2, one ridge 122 is shown as the region between two adjacent lines, and one furrow 123 is shown as a single line. Also, for simplicity, part of the ridge-furrow structure 124 formed in the skin side surface 121 is omitted in FIG. 1. Furthermore, since line B-B shown in FIG. 1 is a line running through the ridge 122, the furrow 123 does not appear in the end view on line B-B (FIG. 4).

This embodiment in which the ridges 122 and furrows 123 extend continuously in a roughly linear manner in the lengthwise direction X is advantageous in that urine supplied to the top sheet 120 readily spreads out in the lengthwise direction X along the ridges 122 and furrows 123, and spreading of urine in the widthwise direction Y, and the consequent leakage of urine from the urine-absorbing pad 100, can be prevented. However, the forms of the ridges 122 and furrows 123 may be modified. As examples of modifications there may be mentioned an embodiment in which the ridges 122 and furrows 123 extend in the widthwise direction Y and are aligned in the lengthwise direction X, an embodiment in which the ridges 122 and furrows 123 extend while varying their directions (for example, in a wavy fashion), and an embodiment in which the ridges 122 and furrows 123 extend intermittently in the lengthwise direction X.

The surfaces of the ridges 122 are curved, and the cross-sectional shapes of the ridges 122 are essentially inverted U-shapes facing the surface. However, the cross-sectional shapes of the ridges 122 may be modified. Examples of modifications include embodiments in which the cross-sectional shapes of the ridges 122 are trapezoidal or triangular. Embodiments in which the ridges 122 are tapered toward the top sections, including this embodiment, are advantageous in that the spaces of the furrows 123 are maintained even when the ridges 122 collapse under force applied to the urine-absorbing pad 100 (for example, body pressure by the wearer).

The ridges 122 have thickness T1, and the furrows 123 have thickness T2. The thickness T1 of the ridges 122 will usually be 0.3 to 1.5 mm, preferably 0.6 to 1.4 mm, and more preferably 0.8 to 1.2 mm, and the thickness T2 of the furrows 123 will usually be 0.1 to 0.5 mm, preferably 0.2 to 0.4 mm and more preferably 0.2 to 0.3 mm. Measurement of the thicknesses of the ridges and furrows is accomplished by the non-contact system described below, using a 100 mm×100 mm top sheet sample cut out from the urine-absorbing pad, and a laser displacement gauge (for example, a Series LJ-G High precision two-dimensional laser displacement gauge (model: LJ-G030) by Keyence Corp.). A sample of the top sheet is placed on a horizontal measuring stage and the displacements of five different ridges from the measuring stage are measured with a laser displacement gauge, recording the average value of the five measured values as the ridge thickness (mm). Similarly, the displacements of five different furrows from the measuring stage are measured with a laser displacement gauge, recording the average value of the five measured values as the furrow thickness (mm).

The ridges 122 have width W1, and the furrows 123 have width W2. The width W1 of the ridges 122 will usually be 2.0 to 5.0 mm and preferably 3.0 to 4.0 mm, and the width W2 of the furrows 123 will usually be 1.0 to 3.0 mm and preferably 1.0 to 2.0 mm. The spacing between every two adjacent ridges 122 will usually be equal to the width W2 of the furrows, and the spacing between every two adjacent furrows 123 will usually be equal to the width of the ridges 122. The width W1 of the ridges 122 is measured as the distance between the border lines between each ridge 122 and the two furrows 123 situated on either side of the ridge, based on a flat photograph or flat image of the top sheet 120 in an unpressed state. The same applies for the width W2 of the furrows 123.

When the widths of the ridges 122 and furrows 123 is smaller than the width of the through-hole or recess of the absorbent body, the top sheet will more easily enter into the through-hole or recess of the absorbent body. This will help ensure the voids of the top sheet, and prevent blocking of the voids of the top sheet by solid components.

For this embodiment the thicknesses and widths of the ridges 122 were approximately the same for each ridge, but ridges may also be present with different thicknesses and widths than the other ridges. The same applies for the thicknesses and widths of the furrows 122.

In the nonwoven fabric used as the top sheet 120, the content of fibers oriented in the thickness direction in the ridges 122 is greater than the content of fibers oriented in the thickness direction in the sections of the nonwoven fabric other than the ridges 122 (for example, the furrows 123). The phrase "fibers oriented in the thickness direction" refers to fibers oriented at an angle of +45 degrees to −45 degrees with respect to the thickness direction Z. The content of thickness oriented fibers in the ridges 122 is preferably 55 to 100% and more preferably 60 to 100%. The difference between the content of thickness oriented fibers in the ridges 122 and the content of fibers oriented in the thickness direction at sections of the nonwoven fabric other than the ridges 122 (for example, the furrows 123) is preferably 10 to 100% and more preferably 20 to 100%.

The method of measuring the content of fibers oriented in the thickness direction in prescribed sections of the nonwoven fabric is as follows.

(1) The nonwoven fabric is cut to prepare a nonwoven fabric sample.

(2) A VHX-100 digital microscope by Keyence Corp. is used to photograph a magnified image of the cut surface of the nonwoven fabric sample from the perpendicular direction. The magnified image is an image magnified to a factor allowing 50 or more fibers to be measured, and the magnification factor may be 20× to 50×, for example. When the magnified image is taken, the focus is directed toward the foremost fibers in the cut surface of the nonwoven fabric sample (disregarding fibers that have irregularly protruded forward), for setting of the photographic depth. The magnified image is reproduced on a PC screen as a 3D image.

(3) The 3D image is converted to a 2D image, multiple lines extending parallel to the thickness direction of the nonwoven fabric sample are drawn on the 2D image, and the number of fibers oriented at angles of +45 degrees to −45 degrees with respect to the thickness direction of the nonwoven fabric sample is counted.

(4) The proportion of the number of counted fibers with respect to the total number of fibers in the measurement range is calculated.

(5) Steps (1) to (4) are repeated several times (for example, 3 to 5 times), and the average value is recorded as the content of fibers oriented in the thickness direction.

The wet thickness of the nonwoven fabric used as the top sheet 120 is 85% and preferably at least 90% of the dry thickness of the nonwoven fabric. The method for measuring the dry thickness and wet thickness of the nonwoven fabric is as follows. For measurement of each of the parameters of the nonwoven fabric there is used a nonwoven fabric in a modified state. The modified state of the nonwoven fabric is taking the nonwoven fabric in the dry state and storing it for 24 hours or longer under standard conditions (23±2° C. temperature, 50±5% relative humidity). A nonwoven fabric in the dry state is a nonwoven fabric with a moisture content of usually no greater than 12%, preferably no greater than 10%, and more preferably no greater than 8%.

[Dry Thickness]

Using a thickness gauge (for example, an FS-60DS by Daiei Kagaku Seiki Mfg. Co., Ltd., contact point area: 15 $cm^2$), three different locations of the nonwoven fabric in the modified state (with an area of 15 $cm^2$ at each location when using an FS-60DS thickness gauge) are pressed with a constant pressure of 3 $g/cm^2$, and the thickness after 10 seconds of pressing is measured at each location. The same measurement is conducted for 10 nonwoven fabric sheets, and the average value for the total of 30 measurements is recorded as the dry thickness of the nonwoven fabric.

[Wet Thickness]

Ten test strips (10 mm length×10 mm width) cut out from the nonwoven fabric in the modified state are dipped for 1 hour in distilled water at 20° C. Next, using a thickness gauge (for example, an FS-60DS by Daiei Kagaku Seiki Mfg. Co., Ltd., contact point area: 15 $cm^2$), three different locations of each test strip (with an area of 15 $cm^2$ at the locations when using an FS-60DS thickness gauge) are pressed with a constant pressure of 3 $g/cm^2$, and the thickness after 10 seconds of pressing is measured at each location. The average value for the total of 30 measurements is recorded as the wet thickness of the nonwoven fabric.

The dry thickness of the nonwoven fabric used as the top sheet 120 is preferably 0.6 to 1.6 mm and more preferably 0.8 to 1.4 mm. This is from the viewpoint of preserving the total amount of voids in the top sheet (nonwoven fabric), so that blocking of the top sheet by solid components is inhibited and leakage of urine from the absorbent article is inhibited, even when urine has been absorbed several times.

The basis weight of the nonwoven fabric used as the top sheet 120 is preferably 18 to 40 $g/m^2$ and more preferably 25 to 35 $g/m^2$. This is from the viewpoint of allowing the top sheet (nonwoven fabric) to preserve the voids through which solid components pass, both when dry and when wet.

The method of measuring the basis weight of the nonwoven fabric is as follows. The mass of three test strips (10 mm×10 mm) cut out from the nonwoven fabric in the modified state is measured with a digital balance (for example, an HF-300 electronic scale by Kensei Co., Ltd.), and the mass per unit area ($g/m^2$) of the nonwoven fabric calculated from the average value of the masses of the 3 test strips is recorded as the basis weight of the nonwoven fabric.

A nonwoven fabric in which the ridge-furrow structure 124 has been formed can be produced, for example, by forming a ridge-furrow structure in a web containing thermoplastic resin fibers, and then subjecting it to heat treatment for heat fusion of the crossing sections between the thermoplastic resin fibers in the web. When an air-through nonwoven fabric is to be produced, the heat treatment is carried out by blasting hot air on the web.

The thermoplastic resin composing the thermoplastic resin fibers in the web may be a polyolefin, polyester, polyamide or the like. Examples of polyolefins include straight-chain low-density polyethylene (LLDPE), low-density polyethylene (LDPE), medium-density polyethylene (MDPE), high-density polyethylene (HDPE), polypropylene, polybutylene, and copolymers composed mainly of the foregoing (for example, ethylene-vinyl acetate copolymer (EVA), ethylene-ethyl acrylate copolymer (EEA), ethylene-acrylic acid copolymer (EAA) or an ionomer resin). Examples of polyesters include polyesters of straight-chain or branched polyhydroxyalkane acids up to C20, such as polyethylene terephthalate (PET), polytrimethylene terephthalate (PTT), polybutylene terephthalate (PBT), polylactic acid and polyglycolic acid, copolymers composed mainly thereof, and copolymerized polyesters composed mainly of alkylene terephthalates copolymerized with a small amount of another component. Examples of polyamides include 6-nylon and 6,6-nylon.

The thermoplastic resin fibers themselves are preferably hydrophobic. This is from the viewpoint of preventing leakage by the absorbent article.

The thermoplastic resin fibers may be composed of a single type of thermoplastic resin, but preferably they are composite fibers comprising two or more different thermoplastic resins. Preferred composite fibers are core-sheath composite fibers. The thermoplastic resin forming the sheath component of core-sheath composite fibers is selected as a thermoplastic resin with a melting point that is lower than the melting point of the thermoplastic resin forming the core component. Examples of thermoplastic resins forming the core component and sheath component of core-sheath composite fibers include olefin-based resins such as polyethylene and polypropylene, polyamide-based resins such as nylon, and polyester-based resins, polyacrylonitrile-based resins and the like. The thermoplastic resin forming the sheath component is preferably polyethylene (for example, high-density polyethylene, low-density polyethylene, linear low-density polyethylene, or a mixture of such types of polyethylene), and the thermoplastic resin forming the core component is preferably polypropylene or polyester.

The method used to form the ridge-furrow structure in the web may be any of the methods described in, for example, Japanese Unexamined Patent Publication No. 2008-25079, Japanese Unexamined Patent Publication No. 2008-23326 and Japanese Unexamined Patent Publication No. 2009-30218. According to these methods, the web is placed on an air-permeable supporting member (for example, a net-like supporting member), and the air-permeable supporting member is moved in a prescribed direction while spraying a gas (usually air) continuously onto the top side of the web, to form a ridge-furrow structure in the web. The bottom side of the web has a form following the form of the air-permeable supporting member. For example, when the web-mounting side of a net-like supporting member is flat, the bottom side of the web will be essentially flat (and therefore the bottom side of the nonwoven fabric will also be essentially flat).

The region of the top side of the web on which the gas has been sprayed has furrows formed extending in the movement direction of the air-permeable supporting member, with ridges being formed between every two adjacent furrows. During this time, the fibers in the regions that have been sprayed with gas migrate to both sides of the furrows, so that the basis weight of the ridges will generally be higher than the basis weight of the furrows. In addition, the gas that has impacted the non-gas-penetrable sections of the air-permeable supporting member (for example, the wires) and have been repelled causes the fibers in the web to curl upward, and the content of fibers oriented in the thickness direction at the ridges within the ridge-furrow structure formed in the web is greater than the content of fibers oriented in the thickness direction at the other sections (for example, the furrows). The number of ridges and furrows, as well as their spacing, basis weights, fiber densities, contents of fibers oriented in the thickness direction, etc. may be adjusted within the desired range by adjusting the number of nozzles, the orifice diameter and pitch, the temperature and spray volume of the gas sprayed from the nozzle, the tension of the web, and the like.

Figure 12:
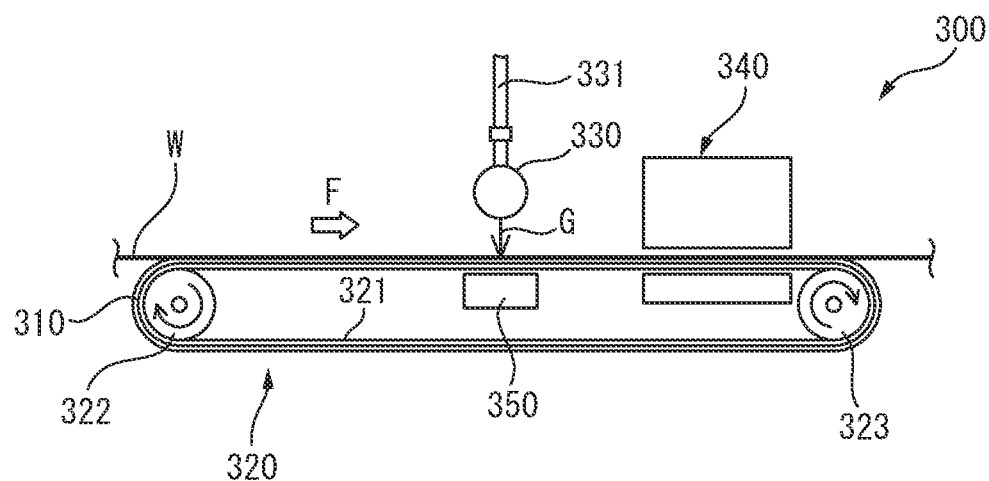
FIG. 12(A) is an overview of a nonwoven fabric production apparatus.
FIG. 12(B) is a magnified perspective view of the sprayer of a nonwoven fabric production apparatus.
Figure 12:
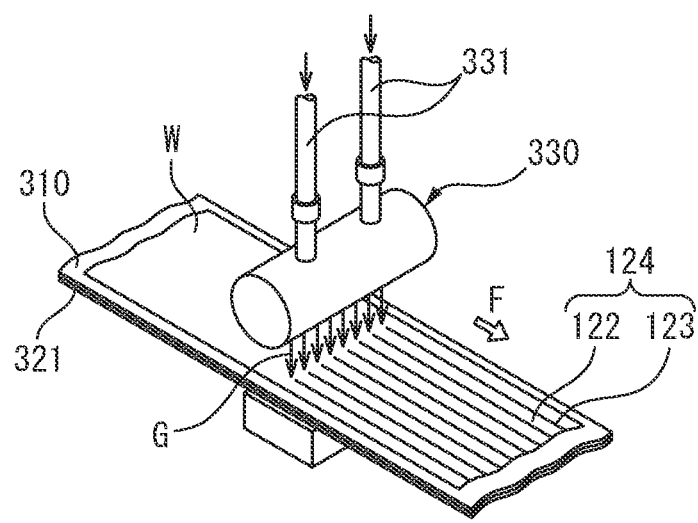
Figure 13:
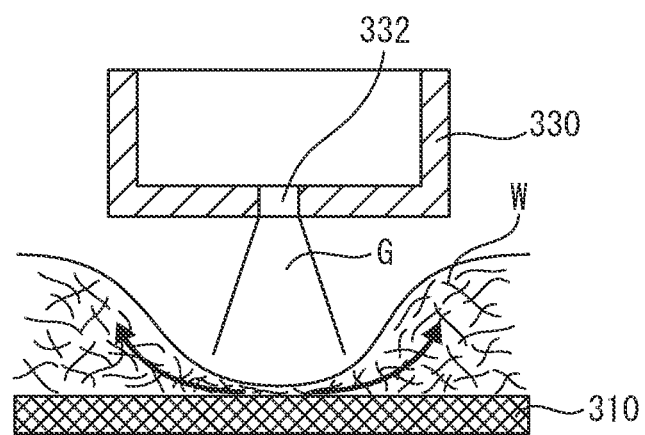
FIG. 13 is a diagram illustrating the action of gas sprayed from a sprayer onto a web.

FIG. 12 and FIG. 13 are diagrams illustrating an embodiment of a nonwoven fabric production apparatus for production of a nonwoven fabric having a ridge-furrow structure 124 formed therein. FIG. 12(A) is an overview of the nonwoven fabric production apparatus 300, FIG. 12(B) is a magnified perspective view of the sprayer 330 of the nonwoven fabric production apparatus 300, and FIG. 13 is a diagram illustrating the action of gas sprayed from the sprayer 330 onto the web W.

The nonwoven fabric production apparatus 300 comprises an air-permeable supporting member 310 that supports the web W, a conveyor 320 that conveys the air-permeable supporting member 310 in a prescribed direction F, a sprayer 330 that sprays gas onto the surface of the web W supported on the air-permeable supporting member 310, and a heater unit 340 that performs heat treatment of the web W after gas spray treatment.

The air-permeable supporting member 310 is a net-like supporting member that is formed by interweaving a plurality of wires of prescribed thickness, which are the non-gas-penetrable sections. By interweaving of the plurality of wires across prescribed spacings in the air-permeable supporting member 310, a plurality of holes are formed as the gas-penetrable sections. The holes allow gas G sprayed from the sprayer 330 to penetrate downward.

The conveyor 320 comprises a gas-permeable belt section 321 that supports the air-permeable supporting member 310, and rotating parts 322, 323 that rotate the gas-permeable belt section 321 in a prescribed direction.

The sprayer 330 is connected in a gas-flowable manner to a gas supply unit (not shown), via a gas line 331. A plurality of spray openings 332 are formed at prescribed spacings in the sprayer 330. The gas G supplied from the gas supply unit (not shown) to the sprayer 330 through the gas line 331 is sprayed in a continuous manner on the top side of the web W supported on the air-permeable supporting member 310, from the plurality of spray openings 332 formed in the sprayer 330. The gas G that has passed through the air-permeable supporting member 310 is suctioned by an aspirator 350 situated below the sprayer 330.

As the gas G sprayed from the spray opening 332 is repelled upon impacting with the non-gas-penetrable sections (wires) of the air-permeable supporting member 310, the fibers in the web W curl upward and the orientation of the web W in the thickness direction is increased (see FIG. 13). This results in a greater content of fibers oriented in the thickness direction at the ridges than the content of fibers oriented in the thickness direction at the furrows, within the ridge-furrow structure formed in the web W.

The temperature of the gas G sprayed from the spray opening 332 may be ordinary temperature, but from the viewpoint of improving the moldability of the ridge-furrow structure, it is at or above the softening point of the thermoplastic resin fibers composing the web W, and preferably in the range of +50° C. to −50° C. from the melting point.

The web W supported on the air-permeable supporting member 310 is subjected to heat treatment with a heater unit 340 after the gas spray treatment. The web W supported on the air-permeable supporting member 310 is continuously conveyed so as to reside for a prescribed time in the heating space formed inside the heater unit 340. The heat treatment with the heater unit 340 causes heat fusion of the crossing sections between the thermoplastic resin fibers in the web W while preserving the ridge-furrow structure formed in the web W, thereby producing a nonwoven fabric with a ridge-furrow structure 124 formed therein.

The nonwoven fabric used as the top sheet 120 has a first fiber layer with a skin side surface 121 and a second fiber layer located further toward the absorbent body 140 than the first fiber layer.

The mean fiber size of the first fiber layer is preferably smaller than the mean fiber size of the second fiber layer. This will improve the feel on the skin of the top sheet 120 on the skin side surface 121. The mean fiber size in the first fiber layer is preferably 1.3 to 3.3 dtex, and the mean fiber size in the second fiber layer is preferably 2.3 to 4.4 dtex.

The mean fiber length of the fibers in the first fiber layer is preferably 30 to 55 mm, and the mean fiber length of the fibers in the second fiber layer is preferably 30 to 55 mm.

The first fiber layer and second fiber layer preferably include concentric core-sheath composite fibers. Preferably, the second fiber layer contains eccentric core-sheath composite fibers and the first fiber layer contains no eccentric core-sheath composite fibers. Because eccentric core-sheath composite fibers tend to exhibit spiral crimping upon heating, the presence of eccentric core-sheath composite fibers in the second fiber layer as the lower layer allows the bulk and voids to be preserved even under body pressure on the top sheet or the load produced by absorption of urine and the like. As a result, this prevents blocking of the voids of the top sheet by solid components, avoiding inhibition of permeation by urine and minimizes leakage of urine from the absorbent article. When the second fiber layer contains eccentric core-sheath composite fibers, their content is preferably 10 mass % to 100 mass % of the second fiber layer, and more preferably 50 mass % to 100 mass % of the second fiber layer.

The first fiber layer is composed of fibers with durable hydrophilicity, while the second fiber layer is composed of fibers with durable hydrophilicity and fibers with non-durable hydrophilicity. Combining these fiber chemical properties with the specific nonwoven fabric structure described above renders the absorbent article resistant to leakage.

Since the first fiber layer contains fibers with durable hydrophilicity, urine supplied onto the surface of the top sheet is drawn into the first fiber layer interior. When the urine drawn into the first fiber layer then contacts with the second fiber layer, it tends to rapidly migrate into the absorbent body together with the non-durable hydrophilic components of the fibers with non-durable hydrophilicity, present in the second fiber layer, while preserving the solid components.

In the second fiber layer, increasing frequency of urine absorption causes more non-durable hydrophilic components to migrate into the absorbent body together with the urine, and therefore the resin composing the fibers with non-durable hydrophilicity (the thermoplastic resin) becomes exposed. The thermoplastic resin is more hydrophobic than the non-durable hydrophilic component, and since the solid components in the urine are less prone to adhering onto the fibers in the second fiber layer, the solid components tend to more easily migrate into the absorbent body. This is because the solid components in the urine tend to have hydrophilic surfaces.

The fibers with durable hydrophilicity in the second fiber layer serve the role of drawing in urine from the first fiber layer to the second fiber layer when the absorbent article has repeatedly absorbed urine. When the second fiber layer does not contain fibers with durable hydrophilicity, increasing frequency of urine absorption results in exposure of the resin composing the fibers (the thermoplastic resin) in the second fiber layer, such that the second fiber layer exhibits hydrophobicity, thus reducing uptake of urine by the second fiber layer.

Furthermore, when the second fiber layer does not contain fibers with non-durable hydrophilicity, for example, when the second fiber layer contains only fibers with durable hydrophilicity, urine supplied to the surface of the top sheet is readily taken up into the first fiber layer and the second fiber layer, but the urine pools in the first fiber layer and the second fiber layer and is less likely to migrate into the absorbent body. In addition, the solid components in the urine readily adhere onto the fibers with durable hydrophilicity, tending to cause blocking of the top sheet by the solid components.

Throughout the present specification, the term "fibers with durable hydrophilicity" is defined as fibers having an evaluation score of 45/50 or greater in the initial hydrophilicity evaluation test described hereunder, and an evaluation score of 45/50 or greater in the durable hydrophilicity evaluation test described hereunder.

Also, the first fiber layer and/or second fiber layer in the absorbent article of the invention may contain two or more different types of fibers with durable hydrophilicity. In such cases, a small difference between the evaluation score in the initial hydrophilicity evaluation test and the evaluation score in the durable hydrophilicity evaluation test is evaluated as higher durable hydrophilicity.

Throughout the present specification, the term "fibers with non-durable hydrophilicity" is defined as fibers having an evaluation score of 45/50 or greater in the initial hydrophilicity evaluation test described hereunder, and an evaluation score of less than 45/50 in the durable hydrophilicity evaluation test described hereunder.

Also, the second fiber layer in the absorbent article of the invention may contain two or more different types of fibers with non-durable hydrophilicity. In such cases, a large difference between the evaluation score in the initial hydrophilicity evaluation test and the evaluation score in the durable hydrophilicity evaluation test is evaluated as higher non-durable hydrophilicity, or in other words, lower durable hydrophilicity.

[Initial Hydrophilicity Evaluation Test]

(1a) The fibers to be evaluated are passed through a carding machine to form a web, a nonwoven fabric with a basis weight of 30 g/m$^2$ is produced from the web, and a 10 cm×10 cm sample is cut out from the nonwoven fabric.

(1b) The sample is placed on 10 sheets of filter paper cut to a size of 12 cm×12 cm, and a burette is set with the dropping orifice situated at a height of 1 cm from the surface of the sample.

(1c) One droplet (approximately 0.05 mL) of deionized water is dropped from the burette onto the sample, and the disappearance time is measured as the time from dropping of the droplet until its disappearance.

(1d) The burette dropping test of (1c) is repeated at a total of 50 different locations, and the number n with a disappearance time of less than 3 seconds is calculated, and n/50 is recorded as the evaluation score.

The test is conducted in a thermostatic chamber at 20° C.

[Durable Hydrophilicity Evaluation Test]

(2a) The fibers to be evaluated are passed through a carding machine to form a web, a nonwoven fabric with a basis weight of 30 g/m$^2$ is produced from the web, and a 10 cm×10 cm sample is cut out from the nonwoven fabric.

(2b) The sample is placed on a wire mesh, a cylinder with an inner diameter of 6 cm is placed on the sample, and 70 mL of deionized water is poured into the cylinder.

(2c) The sample is allowed to stand for 3 minutes after rinsing with deionized water, and then the sample is sandwiched between 10 sheets of filter paper cut to a size of 12 cm×12 cm, an acrylic board with a size of 12 cm×12 cm is placed thereover, a 4 kg weight is placed on the acrylic board, and the sample is dewatered for 5 minutes.

(2d) Following the dewatering, the sample is air-dried for 1 hour.

(2e) The burette dropping test of (1c) and (1d) is carried out at the section of the sample where the deionized water has penetrated.

The test is conducted in a thermostatic chamber at 20° C.

Both the fibers with durable hydrophilicity and the fibers with non-durable hydrophilicity initially, that is in the non-load-applied state, have a water contact angle of preferably 25 to 80° and more preferably 30 to 70°. These ranges are from the viewpoint of the effect of the invention.

The fibers with durable hydrophilicity and the fibers with non-durable hydrophilicity, after being dipped in deionized water for 20 minutes, sandwiched between two filter paper sheets for dewatering and then allowed to dry naturally for 1 hour, have a water contact angle of preferably 60° or smaller and larger than 60°, and more preferably 55° or smaller and larger than 75°.

These ranges are from the viewpoint of the effect of the invention.

The water contact angle is measured in the following manner.

(1) An MCA-J Automatic microscopic contact angle meter by Kyowa Interface Science Co., Ltd. is prepared.

(2) A minute droplet (20 pL) discharged from an ink-jet is dropped onto a fiber to be measured, and the condition of the droplet is video recorded over time.

(3) The image immediately after adhesion of the minute droplet onto the fiber is subjected to image analysis, and the contact angle of the minute droplet with respect to the fiber is calculated.

(4) The contact angle is the average value of measurements at a total of 20 locations on 20 different fibers.

The fibers with durable hydrophilicity and the fibers with non-durable hydrophilicity are not particularly restricted so long as they conform to the definitions given above, and for example, they can be formed by coating or kneading a durable hydrophilic agent and a non-durable hydrophilic agent, respectively, in the fibers.

There are no particular restrictions on the durable hydrophilic agent and non-durable hydrophilic agent, and any one that is coated onto or kneaded into fibers in the technical field may be employed. Examples of non-durable hydrophilic agents include alkyl phosphate ester salts, alkyl phosphate metal salts and the like. Examples of durable hydrophilic agents include C10 to 30 alkyl phosphate ester salts and mixtures of C10 to 30 betaine compounds with sulfates or sulfonates, or mixtures of alkyl phosphate ester salts with polyether-modified silicones.

The nonwoven fabric contains the first fiber layer and the second fiber layer in proportions of preferably 20 to 80 mass % and 80 to 20 mass %, more preferably 30 to 70 mass % and 70 to 30 mass %, and even more preferably 35 to 65 mass % and 65 to 35 mass %, respectively. This is from the viewpoint of rapid migration of urine into the absorbent body together with the solid components.

The second fiber layer contains fibers with durable hydrophilicity and fibers with non-durable hydrophilicity in proportions of preferably 20 to 80 mass % and 80 to 20 mass %, more preferably 30 to 70 mass % and 70 to 30 mass % and even more preferably 35 to 65 mass % and 65 to 35 mass %, respectively, with respect to the total mass. This is also from the viewpoint of rapid migration of urine into the absorbent body together with the solid components.

The durable hydrophilicity of the first fiber layer is preferably greater than the durable hydrophilicity of the second fiber layer. Since the hydrophilicity of the second fiber layer will thereby tend to be reduced more than the hydrophilicity of the first fiber layer when urine has been repeatedly supplied to the urine-absorbing pad 100, rewetting of urine absorbed into the absorbent body 140 from the second fiber layer to the first fiber layer will be minimized.

The durable hydrophilicity of the first fiber layer and the durable hydrophilicity of the second fiber layer are measured in the following manner.

(1) An acrylic cylinder with an inner diameter of 10 mm is prepared.

(2) The cylinder is placed on the sample (first fiber layer or second fiber layer), and deionized water containing 10 mL of added dye (1st time) is dropped into the cylinder over a period of about 5 seconds.

(3) The sample is dried at 50° C. for 30 minutes.

(4) The cylinder is again placed on the location of the dried sample where the deionized water (1st time) was dropped).

(5) Deionized water containing 10 mL of added dye (2nd time) is dropped into the cylinder over a period of about 5 seconds, and the liquid permeation time, from the start of dropping until the deionized water permeated the sample, is measured.

A shorter liquid permeation time represents higher durable hydrophilicity.

The ridges 122 for this embodiment (the elevated sections extending in the lengthwise direction X) are only examples of projections, and the types of projections formed on the skin side surface 121 of the top sheet 120 may be modified. As a modified example there may be mentioned an embodiment in which a nonwoven fabric having a skin side surface with a plurality of projections formed in an interspersed manner is used as the top sheet 120. In a nonwoven fabric having a skin side surface with a plurality of projections formed in an interspersed manner, the thickness of the sections where the projections have been formed (the distance from the bottom side of the nonwoven fabric to the top sections of the projections), the thickness of sections where the projections have not been formed (the recesses) (the distance from the bottom side of the nonwoven fabric to the deepest parts of the recesses), the pitch of the projections (the distance between the top sections of two adjacent projections), etc., are appropriately modified in consideration of the function of the irregular structure (for example, increasing the liquid permeability or improving the feel on the skin). The method of producing a nonwoven fabric having a skin side surface with a plurality of projections formed in an interspersed manner may be a method utilizing gear stretching, a method utilizing heat stretching of heat-extendable fibers and/or heat shrinkage of heat-shrinkable fibers, or the like. In a method utilizing heat stretching of heat-extendable fibers and/or heat shrinkage of heat-shrinkable fibers, the content of fibers oriented in the thickness direction at the ridges in the ridge-furrow structure formed in the nonwoven fabric can potentially be greater than the content of fibers oriented in the thickness direction at the other sections (for example, the furrows).

An example of a method utilizing gear stretching is a method in which a first nonwoven fabric layer is shaped with projections and recesses by gear stretching, after which it is partially joined with a second nonwoven fabric layer at the sections other than the projections, to produce a nonwoven fabric having a skin side surface with a plurality of projections formed in an interspersed manner.

An example of a method of utilizing heat stretching of heat-extendable fibers and heat shrinkage of heat-shrinkable fibers is a method in which heat treatment is carried out on a laminated sheet having a heat-extendable fiber layer on the skin side and having a heat-shrinkable fiber layer partially joined to the heat-extendable fiber layer by joining sections, on the clothing side, and the heat-extendable fiber layer is caused to bulge on the skin side by heat stretching of the heat-extendable fiber layer and heat shrinkage of the heat-shrinkable fiber layer, thereby producing a nonwoven fabric having a skin side surface with a plurality of projections formed therein.

An example of a method utilizing heat shrinkage of heat-shrinkable fibers is a method in which heat treatment is carried out on a laminated sheet having a non-heat-shrinkable fiber layer on the skin side and having a heat-shrinkable fiber layer partially joined to the non-heat-shrinkable fiber layer by joining sections, on the clothing side, and the non-heat-shrinkable fiber layer is caused to bulge on the skin side by heat shrinkage of the heat-shrinkable fiber layer, thereby producing a nonwoven fabric having a skin side surface with a plurality of projections formed therein.

An example of a method utilizing heat stretching of heat-extendable fibers is a method in which heat treatment is carried out on a laminated sheet having a heat-extendable fiber layer on the skin side and having a non-heat-extendable fiber layer partially joined to the heat-extendable fiber layer by joining sections, on the clothing side, and the heat-extendable fiber layer is caused to bulge on the skin side by heat stretching of the heat-extendable fiber layer, thereby producing a nonwoven fabric having a skin side surface with a plurality of projections formed therein.

The absorbent body 140 is disposed between the top sheet 120 and the back sheet 130, and extends from the abdomen side section 111 through the crotch section 112 up to the back side section 113.

The absorbent body 140 has a first absorbing layer 140a and a second absorbing layer 140b. However, the number of layers of the absorbent body 140 may be modified. As a modified example, there may be mentioned an embodiment in which the absorbent body 140 is composed of a single layer, or an embodiment in which the absorbent body 140 has one, two or more layers in addition to the first absorbing layer 140a and the second absorbing layer 140b.

The first absorbing layer 140a and second absorbing layer 140b of the absorbent body 140 include an absorbent material capable of absorbing urine discharged by the wearer. The absorbent material may be, for example, hydrophilic fibers, an absorbent polymer or the like. Examples of hydrophilic fibers include wood pulp; nonwood pulp; regenerated celluloses such as rayon or fibril rayon; and semi-synthetic celluloses such as acetate or triacetate. Examples of absorbent polymers include polyacrylic acid salt-based, polysulfonic acid salt-based, maleic anhydride salt-based, polyacrylamide-based, polyvinyl alcohol-based and polyethylene oxide-based super-absorbent polymers (SAP), and the like.

The shape of the first absorbing layer 140a as viewed flat is a gourd-shaped that is narrowed at the approximate center in the lengthwise direction, and the shape of the second absorbing layer 140b as viewed flat is essentially rectangular. This will allow the narrowed section of the absorbent body 140 to fit more easily in the crotch of the wearer. However, the shape of the absorbent body 140 as viewed flat may be modified.

The thickness, basis weight etc. of the first absorbing layer 140a and the second absorbing layer 140b are appropriately adjusted in consideration of the liquid absorbing and other properties of the absorbent body 140. The thickness of the first absorbing layer 140a will usually be 1.5 to 5.0 mm and preferably 2.5 to 3.5 mm, and the basis weight will usually be 150 to 400 g/m$^2$ and preferably 200 to 300 g/m$^2$. The thickness of the second absorbing layer 140b will usually be 1.5 to 5.0 mm and preferably 2.5 to 3.5 mm, and the basis weight will usually be 150 to 400 g/m$^2$ and preferably 200 to 300 g/m$^2$. The thickness of an absorbent body is measured in the following manner, using a 100 mm×100 mm absorbent body sample cut from the urine-absorbing pad, and a commercially available thickness gauge (for example, a JA257 by Peacock, measuring surface: 50 mm (diameter), measuring pressure: 3 g/cm$^2$). The thickness gauge is pressed on 5 different locations of an absorbent body sample at a constant pressure of 3 g/cm$^2$, and the thickness at each location after 10 seconds of pressure is measured, recording the average value of the 5 measurements as the thickness (mm).

The maximum width of the second absorbing layer 140b, which is located more to the back sheet 130 side than the first absorbing layer 140a, is smaller than the minimum width of the first absorbing layer 140a. That is, the absorbent body 140 has a high basis weight section formed by a region where the first absorbing layer 140a and the second absorbing layer 140b overlap, and low basis weight sections formed by regions of the first absorbing layer 140a that do not overlap with the second absorbing layer 140b, the low basis weight sections extending in the lengthwise direction X. Incidentally, "high basis weight" and "low basis weight" mean relatively high and low basis weight. The widths of the first absorbing layer 140a and the second absorbing layer 140b may be modified.

In this embodiment in which the first absorbing layer 140a with the larger size is located more toward the top sheet 120 than the second absorbing layer 140b with the smaller size, the wearer feels less of a level difference due to the difference in sizes of the first absorbing layer 140a and second absorbing layer 140b, thereby improving the feel of the urine-absorbing pad 1 when it is worn. However, the positional relationship of the first absorbing layer 140a and the second absorbing layer 140b may be modified. An example of a modification is an embodiment in which the second absorbing layer 140b is located more toward the top sheet 120 than the first absorbing layer 140a.

Since the second absorbing layer 140b has a smaller maximum length than the minimum length of the first absorbing layer 140a, and both ends in the lengthwise direction X of the absorbent body 140 are low basis weight sections, the absorbent body 140 easily folds at the folding line extending in the widthwise direction Y (for example, both edges in the lengthwise direction of the high basis weight section and both edges in the lengthwise direction of the low basis weight sections). On the other hand, the top sheet 120 having ridges 122 formed extending in the lengthwise direction X are resistant to folding on the folding line extending in the widthwise direction Y. If the top sheet 120 thus overlaps with the absorbent body 140 in the thickness direction Z, the absorbent body 140 will be resistant to folding on the folding line extending in the widthwise direction Y. This will improve the feel of the absorbent article 100 for the wearer when it is worn.

The first absorbing layer 140a and second absorbing layer 140b may be covered by a core wrap. If the first absorbing layer 140a and second absorbing layer 140b, which are laminar molded articles of absorbent materials, are covered with a core wrap, then it will be possible to prevent disintegration of the first absorbing layer 140a and second absorbing layer 140b. The liquid-permeable sheet to be used as the core wrap may be a nonwoven fabric, for example.

In the first absorbing layer 140a there is formed a through-hole 141 running through the first absorbing layer 140a in the thickness direction Z, and in the second absorbing layer 140b there is formed a through-hole 141b running through the second absorbing layer 140b in the thickness direction Z. The through-holes 141a, 141b are located in the crotch section 112 of the urine-absorbing pad 100, while extending in the lengthwise direction X through the center of the absorbent body 140 in the widthwise direction Y. The first absorbing layer 140a and second absorbing layer 140b are layered in such a manner that the locations of the through-holes 141a, 141b match (that is, the through-holes 141a, 141b are mutually communicating). Thus, in the absorbent body 140, a through-hole 141 running through the absorbent body 140 in the thickness direction Z is formed by through-holes 141a, 141b. Similar to the through-holes 141a, 141b, the through-hole 141 is located in the crotch section 112 of the urine-absorbing pad 100, while extending in the lengthwise direction X through the center of the absorbent body 140 in the widthwise direction Y. Consequently, the location of the through-hole 141 easily matches the location of the genitals (urinary excretion orifice) of the wearer, thereby improving the fitting property of the urine-absorbing pad 100 for the wearer. Moreover, because the section that contacts with the genitals (urinary excretion orifice) of the wearer is resistant to becoming moist, this prevents discomfort for the wearer.

Instead of the through-hole 141, there may be formed in the absorbent body 140 a recess that opens to the top sheet 120 side. An absorbent body having a recess that opens to the top sheet 120 side may be formed, for example, by layering the first absorbing layer with a through-hole 141a and a second absorbing layer without a through-hole 141b.

The lengths, widths, etc. of the through-holes 141a, 141b are appropriately adjusted in consideration of the sizes, etc. of the first absorbing layer 140a and the second absorbing layer 140b. The width of the through-hole 141a will generally be 5.0 to 50 mm and is preferably 10 to 20 mm. The width of the through-hole 141b may be equal to or narrower than the width of the through-hole 141a, and it will usually be 5.0 to 40 mm and preferably 10 to 15 mm. The length of the through-hole 141a will usually be 50 to 300 mm, and is preferably 50 to 200 mm and more preferably 50 to 150 mm. The length of the through-hole 141b may be equal to or shorter than the length of the through-hole 141a, and it will usually be 30 to 250 mm and preferably 30 to 150 mm. If the width and length of the through-hole 141a are equal to or greater than the width and length of the through-hole 141b, the size of the through-hole 141 will be kept essentially constant as viewed from the surface of the top sheet 120 side of the absorbent body 140, even with some shifting during the step of layering the first absorbing layer 140a and the second absorbing layer 140b. Furthermore, since a level difference is produced on the inner wall surface of the through-hole 141 and the inner surface area of the through-hole 141 is increased, the urine-absorbing power of the absorbent body 140 is increased at the section where the through-hole 141 has been formed.

In the absorbent body 140 there are formed compressed sections 142, 143 where the absorbent body 140 is compressed in the thickness direction Z, on the outer sides (both sides) of the through-hole 141 in the widthwise direction Y. The compressed sections 142, 143 are where the first absorbing layer 140a and the second absorbing layer 140b are compressed in the thickness direction Z. The compressed sections 142, 143 extend in the lengthwise direction X of the crotch section 112. The compressed sections 142, 143 are recesses opening to the top sheet 120 side, being formed by heat embossing treatment.

The urine-absorbing pad 100 further comprises a fluid-absorbing sheet 160 disposed between the top sheet 120 and the absorbent body 140. The fluid-absorbing sheet 160 is disposed in the region from the crotch section 112 to the back side section 113, in such a manner as to not overlap with the through-hole 141 in the thickness direction Z.

The fluid-absorbing sheet 160 has liquid-permeable sheets 161, 162, and an absorbent polymer layer 163 disposed between the liquid-permeable sheets 161, 162. The liquid-permeable sheets 161, 162 are nonwoven fabrics, for example. The nonwoven fabrics may be any of the same examples mentioned for the top sheet 120. The absorbent polymer in the absorbent polymer layer 163 may be any of the same examples mentioned for the absorbent body 140. The basis weight of the absorbent polymer 163 layer is appropriately adjusted in consideration of the urine absorption, etc. desired for the urine-absorbing pad 100. For example, when the liquid-permeable sheets 161, 162 have sizes of 180 mm×130 mm, 2 g of absorbent polymer absorbing 60 g of physiological saline per 1 g may be used to form an absorbent polymer layer 163 with approximately the same size as the liquid-permeable sheets 161, 162.

The absorbent polymer layer 163 has a maximum width $D_1$. The maximum width $D_1$ is the distance between an imaginary straight line extending in the lengthwise direction X through the outermost point on one side in the widthwise direction Y, and an imaginary straight line extending in the lengthwise direction X through the outermost point on the other side in the widthwise direction Y, among the points on the contour line of the absorbent polymer layer 163 in the plane perpendicular to the thickness direction Z in which the absorbent polymer layer 163 is projected. For this embodiment, the width of the absorbent polymer layer 163 is essentially constant.

The second absorbing layer 140b has a smaller maximum width than the minimum width of the first absorbing layer 140a. In the widthwise direction Y of the absorbent article 100, both edges of the absorbent polymer layer 163 are more toward the inner side than both edges of the first absorbing layer 140a, and more toward the outer side than both edges of the second absorbing layer 140b. This can maximize the function as a pressure buffering layer for the top sheet 120, across the region of the top sheet 120 in the widthwise direction that contains at least the entire width of the second absorbing layer 140*b*. Furthermore, this will allow the level difference due to the difference in the sizes of the first absorbing layer 140*a*, the second absorbing layer 140*b* and the absorbent polymer layer 163 to be even less noticeable by the wearer, even after the absorbent polymer layer 163 has absorbed urine and swelled. As a result, the feel of the absorbent article when it is worn can be improved.

In addition, the second absorbing layer 140*b* has a smaller maximum length than the minimum length of the first absorbing layer 140*a*. Both edges of the fluid-absorbing sheet 160 in the lengthwise direction X are located more toward the inner side in the lengthwise direction X than both edges of the second absorbing layer 140*b* in the lengthwise direction X. When the absorbent polymer layer 163 absorbs urine supplied to the absorbent article 100 and swells, the thickness of the absorbent polymer layer 163 increases. However, because both edges of the fluid-absorbing sheet 160 in the lengthwise direction are located more toward the inner side in the lengthwise direction X than both edges in the lengthwise direction X of the second absorbing layer 140*b*, the thinness at both ends in the lengthwise direction X of the absorbent article 100 is ensured even if the thickness of the absorbent polymer layer 163 increases. Consequently, there is a minimal uncomfortable feeling for the wearer that results from increased thickness of the absorbent polymer layer 163 at both ends in the lengthwise direction X of the absorbent article 100. Furthermore, since a nonwoven fabric in which the content of fibers oriented in the thickness direction at the projections is greater than the content of fibers oriented in the thickness direction at the sections other than the projections overlaps with the fluid-absorbing sheet 160 in the thickness direction, there is less of an uncomfortable feeling for the wearer resulting from the thickness difference (level difference) produced at the border between the region where the absorbent polymer layer 163 is present and where it is not present.

The absorbent polymer layer 163 is anchored between the liquid-permeable sheets 161, 162 by an adhesive (for example, a hot-melt adhesive) coated onto at least one of the surfaces of the liquid-permeable sheets 161, 162. From the viewpoint of liquid permeability from the fluid-absorbing sheet 160 to the absorbent body 140, the adhesive is not coated over the entire interface between the liquid-permeable sheets 161, 162, and for example, it is coated in a dotted, spiral, stripe or other pattern.

The absorbent polymer layer 163 may be segmented into a plurality of regions by regions in which the absorbent polymer is not present, extending in any desired direction.

Urine of the elderly (especially bedridden elderly) contains more solid components than the urine of adults in general. Consequently, when the ridges 122 formed in the top sheet 120 are crushed and the bulk of the ridges 122 and the voids are reduced, the solid components in the urine tend to remain in the top sheet 120, causing a reduction in liquid permeability of the top sheet 120. This aspect is advantageous as a urine-absorbing pad for absorption of elderly (especially bedridden elderly) urine, because the urine-absorbing pad 100 easily maintains the bulk of the ridges 122 and the voids.

Due to the force on the inner side in the widthwise direction Y, that is applied when the urine-absorbing pad 100 is worn, the skin side surface 121 of the top sheet 120 readily deforms outward toward the clothing side (back sheet 130 side) with the portions other than the ridges 122 (for example, the furrows 123) as the bending origins, while the absorbent body 140 readily deforms outward toward the skin side (top sheet 120 side). When the urine-absorbing pad 100 is worn, therefore, the top sheet 120 readily enters into the through-hole 141 of the absorbent body 140. Consequently, even when the top sheet 120 is pressed when the urine-absorbing pad 100 is worn, the section of the top sheet 120 that has entered into the through-hole 141 of the absorbent body 140 is resistant to the pressing force, and the shapes of the ridges 122 are easily maintained at that section.

Force directed to the inner side in the widthwise direction Y, which is applied when the urine-absorbing pad 100 is worn, causes the absorbent body 140 to easily deform outward to the skin side, with the compressed sections 142, 143 as bending origins. When the urine-absorbing pad 100 is worn, therefore, the top sheet 120 readily enters into the through-hole 141 of the absorbent body 140. In addition, since the shape of the through-hole 141 of the absorbent body 140 is easily preserved by the compressed sections 142, 143, the space of the through-hole 141 in which the top sheet 120 has entered is also easily maintained.

When the absorbent polymer layer 163 absorbs urine supplied to the urine-absorbing pad 100 and swells, the thickness of the absorbent polymer layer 163 increases. The swelled absorbent polymer layer 163 therefore functions as a pressure buffering layer, and protects the section of the top sheet 120 that does not overlap with the absorbent polymer layer 163 in the thickness direction Z, from pressure. In particular, since the fluid-absorbing sheet 160 is disposed so as not to overlap with the through-hole 141 in the thickness direction Z, the section of the top sheet 120 overlapping with the through-hole 141 in the thickness direction Z is protected from pressure. Consequently, the section of the top sheet 120 overlapping with the through-hole 141 in the thickness direction Z is resistant to pressing force and the shapes of the ridges 122 at that section are easily maintained.

Figure 6:
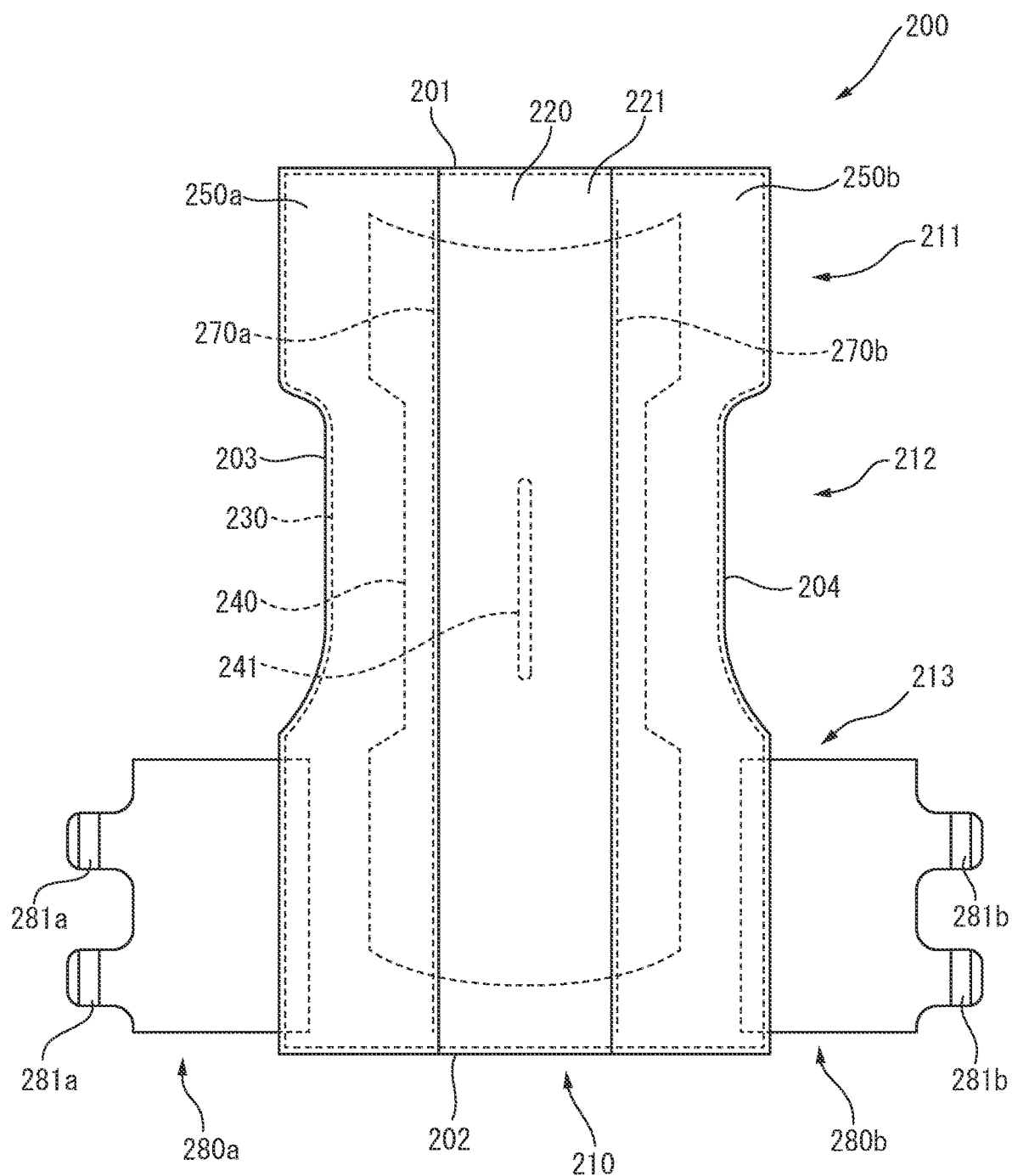
FIG. 6 is a plan view of an exterior body according to an embodiment of the invention.
Figure 7:
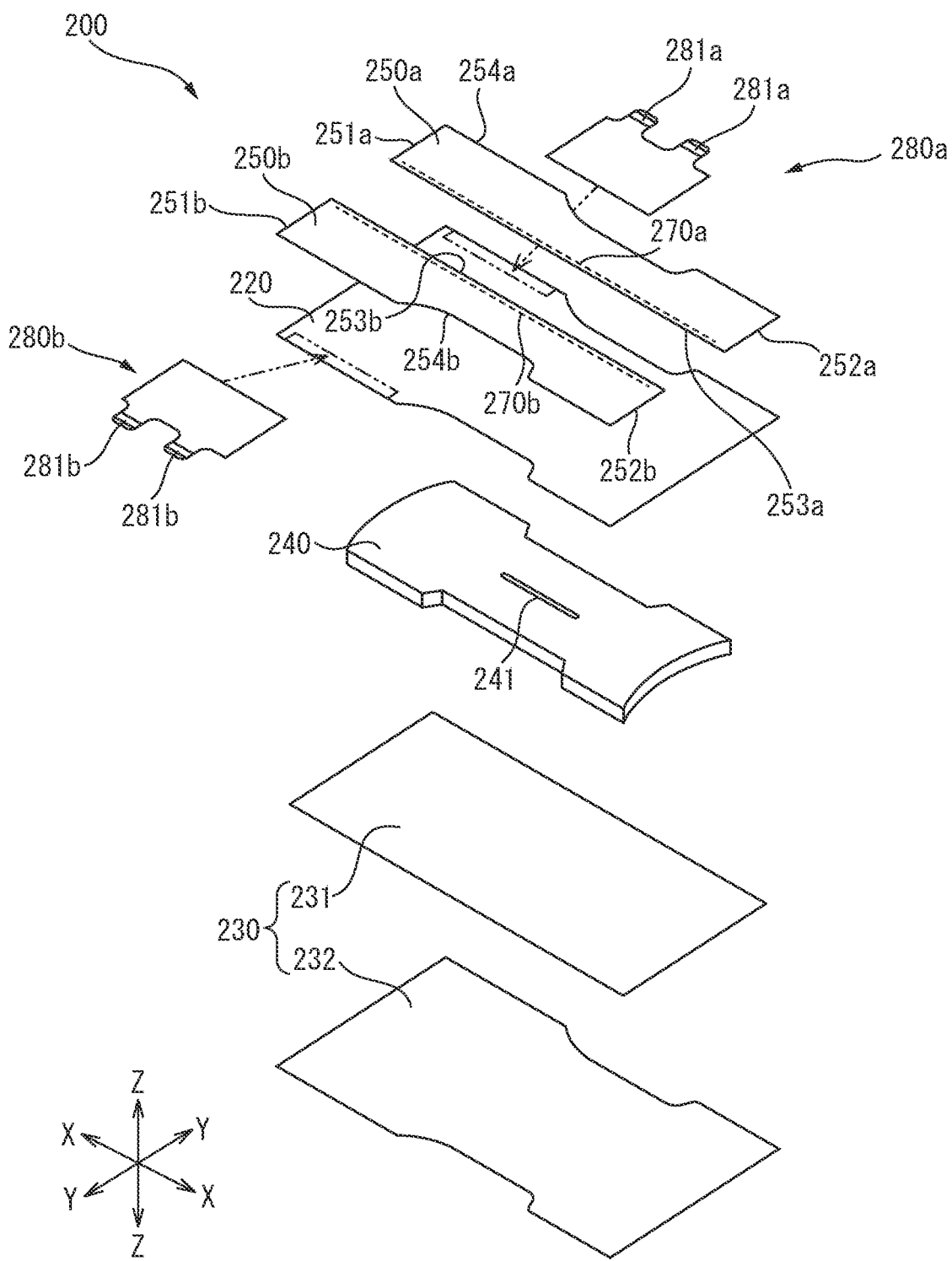
FIG. 7 is an exploded perspective view of the exterior body shown in FIG. 6.
Figure 8:
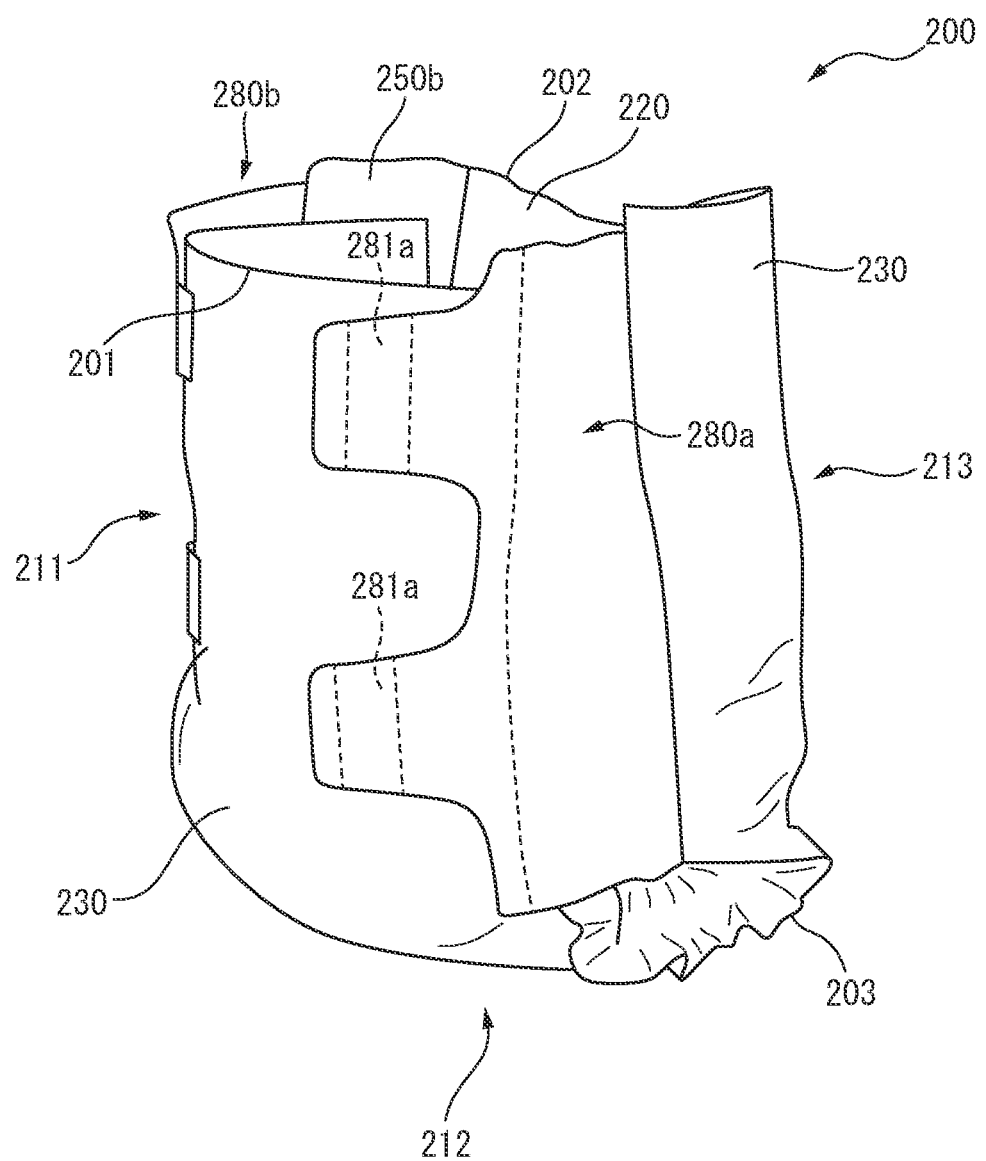
FIG. 8 is a perspective view showing the state of the exterior body of FIG. 6, deformed into the shape of underwear.
Figure 9:
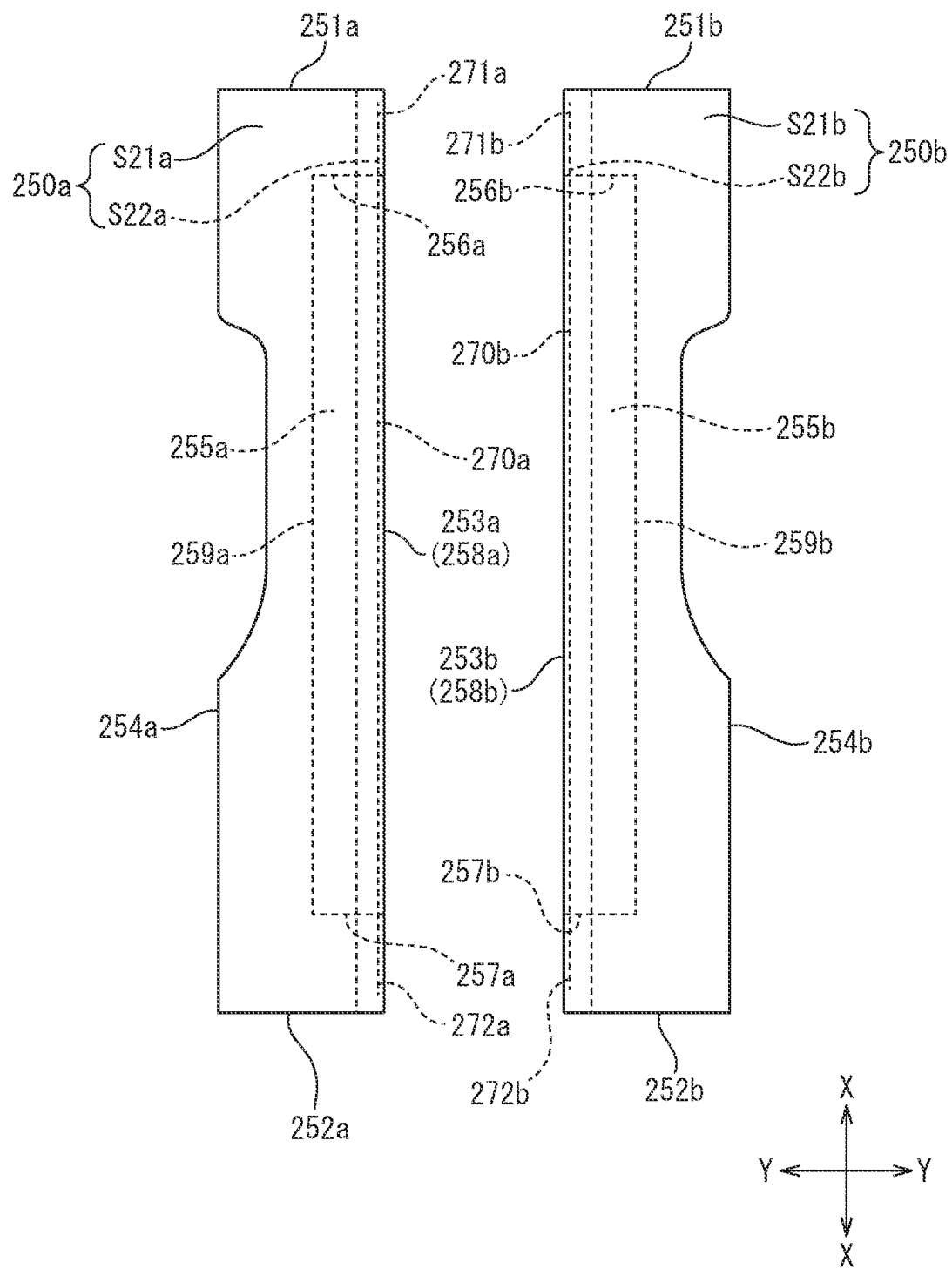
FIG. 9 is a drawing illustrating a side sheet in the exterior body shown in FIG. 6.

An exterior body 200 according to one embodiment of an exterior body of the invention will now be described based on FIG. 6 to FIG. 9. FIG. 6 is a plan view of an exterior body 200, FIG. 7 is an exploded perspective view of the exterior body 200, FIG. 8 is a perspective view of the exterior body 200 deformed into the shape of underwear, and FIG. 9 is an illustration of the side sheets 250*a*, 250*b* of the exterior body 200.

In its spread-out state, the exterior body 200 has a lengthwise direction X, a widthwise direction Y and a thickness direction Z that are mutually orthogonal. The lengthwise direction X, widthwise direction Y and thickness direction Z of the exterior body 200 match the lengthwise direction X, widthwise direction Y and thickness direction Z of the urine-absorbing pad 100.

The exterior body 200 comprises a body section 210 having both edges 201, 202 in the lengthwise direction X and both edges 203, 204 in the widthwise direction Y, and side flap sheets 280*a*, 280*b* extending in the widthwise direction Y from both edges 203, 204 in the widthwise direction Y of the body section 210.

The body section 210 has an abdomen side section 211, a crotch section 212 and a back side section 213, aligned in the lengthwise direction X. The abdomen side section 211 is the section that touches the abdominal region of the wearer, the crotch section 212 is the section that touches the crotch region of the wearer, and the back side section 213 is the section that touches the gluteal region and/or the back region of the wearer. The length of the body section 210 will usually be 650 to 1000 mm, and the width will usually be 300 to 690 mm.

A pair of side flap sheets 280*a*, 280*b* are provided on either side of the back side section 213 of the body section 210. When both edges in the widthwise direction Y of the abdomen side section 211 and both edges in the widthwise direction Y of the back side section 213 are engaged by hook sections 281a, 281b of a mechanical fastener, as engagement means mounted on the side flap sheets 280a, 280b, the exterior body 200 is formed into the shape of underwear, while a waist opening is formed by both edges 201, 202 in the lengthwise direction X of the body section 210, and leg openings are formed by both edges 213, 214 in the widthwise direction Y of the body section 210 (see FIG. 8).

The exterior body 200 can be deformed from its developed form into an underwear form, but alternatively, it may be initially shaped into an underwear form. For example, by joining both edges in the widthwise direction Y of the crotch region 212 and both edges in the widthwise direction Y of the back side section 213, it is possible to shape the exterior body 200 into an underwear form. In this case, the pair of side flap sheets 280a, 280b may be omitted.

The body section 210 is a gourd-shape which is narrowed at approximately the center section in the lengthwise direction X (the section corresponding to the crotch section 212). The crotch section 212 is thus easily fit into the crotch of the wearer. However, the shape of the body section 210 may be appropriately modified in a range that allows deformation into an underwear form.

The body section 210 comprises a liquid-permeable top sheet 220 having a skin side surface 221, a liquid-impermeable back sheet 230 having a clothing side surface 231, a liquid-absorbing absorbent body 240 disposed between the top sheet 220 and the back sheet 230, and liquid-impermeable side sheets 250a, 250b disposed at both edge sections in the widthwise direction Y of the skin side surface 221 of the top sheet 220. However, the absorbent body 240 and the side sheets 250a, 250b may be omitted.

The liquid-permeable sheet used for the top sheet 220 is a nonwoven fabric, for example. The nonwoven fabric may be any of the same examples mentioned for the top sheet 120. The basis weight, thickness, etc. of the top sheet 220 is appropriately adjusted in consideration of the liquid permeability, feel on the skin and the like.

The back sheet 230 has a liquid-impermeable sheet 231 located on the skin side and a liquid-impermeable sheet 232 located on the clothing side. Examples for the liquid-impermeable sheets 231, 232 include waterproof-treated nonwoven fabrics, synthetic resin films, and composite sheets of nonwoven fabrics and synthetic resin films. The thickness, basis weight, etc. of the back sheet 230 is appropriately adjusted in consideration of the liquid impermeability and the like. The back sheet 230 is preferably air-permeable and moisture-permeable in addition to being liquid-impermeable, in order to reduce mustiness during wear.

The absorbent body 240 is disposed between the top sheet 200 and the back sheet 300, and extends from the abdomen side section 211 through the crotch section 212 up to the back side section 213. The shape of the absorbent body 240 as viewed flat is a gourd-shape that narrows at approximately the center in the lengthwise direction X. This will allow the narrowed section of the absorbent body 240 to fit more easily in the crotch of the wearer. The absorbent body 240a includes an absorbent material capable of absorbing urine discharged by the wearer. The absorbent material may be any of the same examples mentioned for the absorbent body 140. The absorbent body 240 may also be covered by a core wrap. The thickness, basis weight, etc. of the absorbent body 240 is appropriately adjusted in consideration of the liquid absorption property and the like. The thickness of the absorbent body 240 will usually be 3 to 10 mm and preferably 4 to 7 mm, and the basis weight will usually be 150 to 500 g/m$^2$ and preferably 200 to 400 g/m$^2$.

In the absorbent body 240 there is formed a through-hole 241 running through the absorbent body 240 in the thickness direction Z. The through-hole 241 is located in the crotch section 212 of the exterior body 200, while extending in the lengthwise direction X through the center of the absorbent body 240 in the widthwise direction Y. Thus, when the urine-absorbing pad 100 is fitted in the exterior body 200, it is easy to match the location of the through-hole 141 of the urine-absorbing pad 100 to the location of the through-hole 241 of the exterior body 200.

Instead of the through-hole 241, there may be formed in the absorbent body 240 a recess that opens to the top sheet 220 side. An absorbent body having a recess that opens to the top sheet 220 side may be formed, for example, by layering a first absorbing layer with a through-hole 241 and a second absorbing layer without a through-hole.

The lengths, widths, etc. of the through-hole 241 are appropriately adjusted in consideration of the size, etc. of the absorbent body 240. The width of the through-hole 241 may be equal to or wider than the width of the through-hole 141, and it will usually be 5 to 50 mm and preferably 15 to 25 mm. The length of the through-hole 241 may be equal to or longer than the length of the through-hole 141, and it will usually be 50 to 700 mm and preferably 90 to 350 mm. Since the width and length of the through-hole 241 are equal to or greater than the width and length of the through-hole 141, it is easy to match the location of the through-hole 141 of the urine-absorbing pad 100 to the location of the through-hole 241 of the exterior body 200 when the urine-absorbing pad 100 is fitted in the exterior body 200.

Examples for the liquid-impermeable sheets to be used as the side sheets 250a, 250b include waterproof treated nonwoven fabrics (for example, point bond nonwoven fabrics, spunbond nonwoven fabrics and spunlace nonwoven fabrics), synthetic resin (for example, polyethylene, polypropylene and polyethylene terephthalate) films, and composite sheets of nonwoven fabrics and synthetic resin films. The thickness, basis weight, etc. of the side sheets 250a, 250b are appropriately adjusted in consideration of the liquid impermeability and the like.

The side sheet 250a has both edges 251a, 252a in the lengthwise direction X and both edges 253a, 254a in the widthwise direction Y, while the side sheet 250b has both edges 251b, 252b in the lengthwise direction X and both edges 253b, 254b in the widthwise direction Y. The side sheets 250a, 250b have leakproof sections 255a, 255b as portions thereof. The leakproof section 255a has both edges 256a, 257a in the lengthwise direction X and both edges 258a, 259a in the widthwise direction Y, while the leakproof section 255b has both ends 256b, 257b in the lengthwise direction X and both ends 258b, 259b in the widthwise direction Y. The edges 253a, 253b of the side sheets 250a, 250b are located nearer than the edges 254a, 254b to the imaginary center line extending in the lengthwise direction X through the center in the widthwise direction Y of the skin side surface 221 of the top sheet 220. The edges 253a, 253b of the side sheets 250a, 250b will also be referred to hereunder as the "near edges" and the edges 254a, 254b as the "far edges". Similarly, the edges 258a, 258b of the leakproof sections 255a, 255b will also be referred to as "near edges" and the edges 259a, 259b as "far edges".

The leakproof sections 255a, 255b are formed within the regions of the side sheets 250a, 250b overlapping with the top sheet 220 in the thickness direction Z, and the near edges 258*a*, 258*b* of the leakproof sections 255*a*, 255*b* match the near edges 253*a*, 253*b* of the side sheets 250*a*, 250*b*.

In the region of the side sheets 250*a*, 250*b* overlapping with the top sheet 220 in the thickness direction Z, the leakproof sections 255*a*, 255*b* are not anchored to the skin side surface 221 of the top sheet 220, but the sections other than the leakproof sections 255*a*, 255*b* are anchored to the skin side surface 221 of the top sheet 220. Consequently, both edges and the far edges 259*a*, 259*b* of the leakproof sections 255*a*, 255*b* in the lengthwise direction X constitute the anchored edges which are anchored to the skin side surface 221 of the top sheet 220, while the near edges 258*a*, 258*b* of the leakproof sections 250*a*, 250*b* are not anchored to the skin side surface 221 of the top sheet 220, and serve as free edges that are separable from the skin side surface 221 of the top sheet 220. The manner of joining the side sheets 250*a*, 250*b* and the top sheet 220 may be, for example, joining by a hot-melt adhesive.

The side sheets 250*a*, 250*b* have first sheet sections S21*a*, S21*b* extending in the widthwise direction Y from the far edges 254*a*, 254*b* to the near edges 253*a*, 253*b*, and second sheet sections S22*a*, S22*b* joined to the first sheet sections S21*a*, S21*b*, being folded over to the top sheet 220 side at the near edges 253*a*, 253*b*. Between the first sheet section S21*a* and the second sheet section S22*a* of the side sheet 250*a*, an elastic member 270*a* extending in the lengthwise direction X along the near edge 253*a* is mounted in a contractible manner in a stretched state, and between the first sheet section S21*b* and the second sheet section S22*b* of the side sheet 250*b*, an elastic member 270*b* extending in the lengthwise direction X along the near edge 253*b* is mounted in a contractible manner in a stretched state. The stretching directions of the elastic members 270*a*, 270*b* approximately match the lengthwise direction X. Both ends 271*a*, 272*a* of the elastic member 270*a* in the lengthwise direction X (stretching direction) extend in the lengthwise direction X beyond both edges 256*a*, 257*a* in the lengthwise direction X of the leakproof section 255*a*, while both edges 271*b*, 272*b* of the elastic member 270*b* in the lengthwise direction X (stretching direction) extend in the lengthwise direction X beyond both edges 256*b*, 257*b* in the lengthwise direction X of the leakproof section 255*b*. Also, both edges 271*a*, 272*a* of the elastic member 270*a* in the lengthwise direction X (stretching direction) are anchored to the top sheet 220 while sandwiched between the first sheet section S21*a* and the second sheet section S22*a*, and both ends 271*b*, 272*b* of the elastic member 270*b* in the lengthwise direction X (stretching direction) are anchored to the top sheet 220 while sandwiched between the first sheet section S21*b* and the second sheet section S22*b*. As a result, the leakproof sections 255*a*, 255*b* can rise up from the skin side surface 221 of the top sheet 220 by the contractive force of the elastic members 270*a*, 270*b*. When the leakproof sections 255*a*, 255*b* rise up from the skin side surface 221 of the top sheet 220, this causes formation of three-dimensional gather sections. When the leakproof sections 255*a*, 255*b* rise up, the far edges 259*a*, 259*b* become base sections, and the near edges 258*a*, 258*b* separate from the skin side surface 221 of the top sheet 220, moving toward the skin side of the wearer. Examples for the elastic members 270*a*, 270*b* include rubber thread, flat rubber and the like.

In the exterior body 200, the skin side surface 221 of the top sheet 220 serves as the fitting side for fitting of the urine-absorbing pad 100. The urine-absorbing pad 100 can be fitted in a detachable manner into the skin side surface 221 of the top sheet 220.

Figure 10:
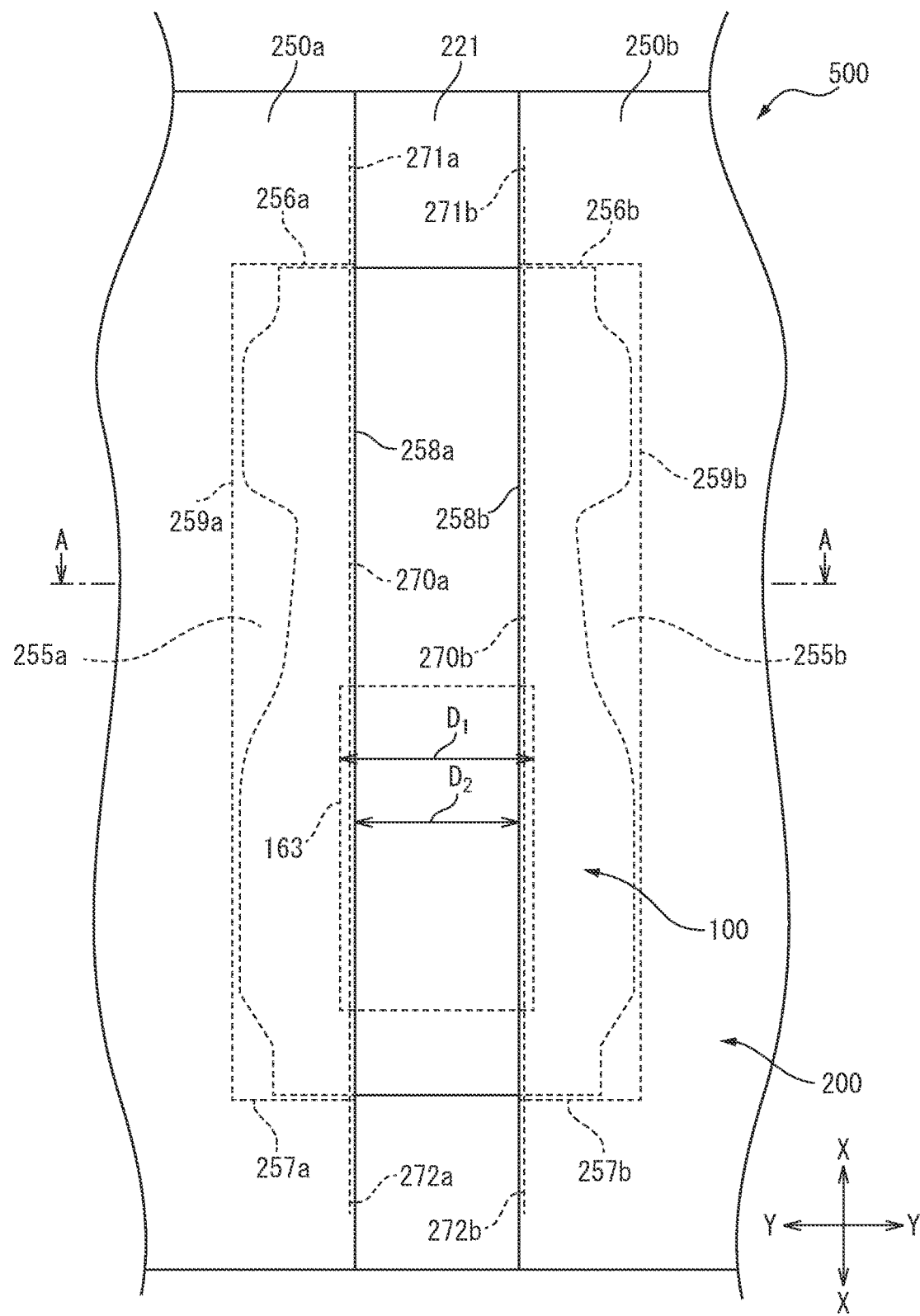
FIG. 10 is a partial enlarged plan view of a wearable article according to an embodiment of the invention.
Figure 11:
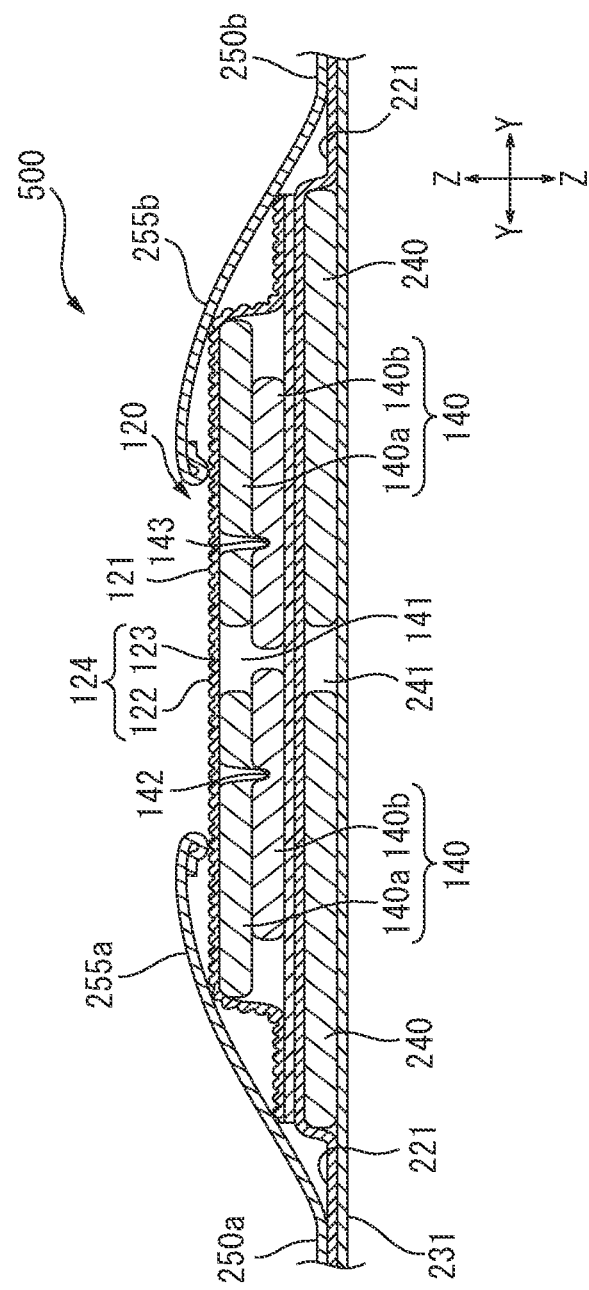
FIG. 11 is a cross-sectional view along line A-A of FIG. 10.

A wearable article 500 according to an embodiment of the wearable article of the invention will now be described based on FIG. 10 and FIG. 11. FIG. 10 is a partial enlarged plan view of the wearable article 500, and FIG. 11 is a cross-sectional view along line A-A of FIG. 10.

The wearable article 500 comprises an exterior body 200, and a urine-absorbing pad 100 fitted in a detachable manner on the fitting side of the exterior body 200 (the skin side surface 221 of the top sheet 220).

The urine-absorbing pad 100 is disposed on the fitting side of the exterior body 200 in such a manner that both edge sections of the urine-absorbing pad 100 in the widthwise direction Y are located between the fitting side of the exterior body 200 (the skin side surface 221 of the top sheet 220) and the leakproof sections 225*a*, 255*b*. When the urine-absorbing pad 100 is fitted into the exterior body, the ridge-furrow structure 124 formed in the top sheet 120 of the urine-absorbing pad 100 serves as marking, for easy positioning of the lengthwise direction X of the urine-absorbing pad 100 and the lengthwise direction X of the exterior body 200.

The maximum width $D_1$ of the absorbent polymer layer 163 of the urine-absorbing pad 100 is greater than the spacing $D_2$ between the elastic member 270*a* and the elastic member 270*b*. When the absorbent polymer layer 163 absorbs urine supplied to the urine-absorbing pad 100 and swells, the leakproof sections 255*a*, 255*b* are pushed upward in the direction in which they rise. Thus, the three-dimensional gather sections formed by rising of the leakproof sections 255*a*, 255*b* are resistant to collapse, and the urine leakage-preventing effect of the three-dimensional gather sections is effectively exhibited.

The spacing $D_2$ between the elastic member 270*a* and the elastic member 270*b* is the spacing between a first imaginary line extending along the fitting side through both edges 271*a*, 272*a* in the lengthwise direction X of the elastic member 270*a*, and a second imaginary line extending along the fitting side through both edges 271*b*, 272*b* in the lengthwise direction X of the elastic member 270*b*. Both edges of the elastic members 270*a*, 270*b* in the lengthwise direction X are disposed so as to be essentially parallel to the first imaginary line and the second imaginary line.

Both edges of the leakproof sections 255*a*, 255*b* in the lengthwise direction X may also approximately match both edges of the urine-absorbing pad 100 in the lengthwise direction. The three-dimensional gather sections formed by rising of the leakproof sections 255*a*, 255*b* are resistant to collapse, and the urine leakage-preventing effect of the three-dimensional gather sections is effectively exhibited.

The through-hole 141 formed in the absorbent body 140 of the urine-absorbing pad 100 overlaps with the through-hole 241 formed in the absorbent body 240 of the exterior body 200, in the thickness direction Z. Consequently, even when the top sheet 120 is pressed when the wearable article 500 is worn, the section of the top sheet 120 that has entered into the through-hole 141 of the absorbent body 140 is resistant to the pressing force, and the shapes of the ridges 122 are easily maintained at that section.

EXAMPLES

Example 1

(1) Production of Web

A web was produced as a layered body of a first fiber layer and a second fiber layer.

The fiber used to compose the first fiber layer was a concentric core-sheath composite fiber A having polyethylene terephthalate as the core component and polyethylene as the sheath component, coated with a durable hydrophilic agent (hereunder referred to as "fiber A"). The mean size of the concentric core-sheath composite fiber A was 2.2 dtex, and the mean fiber length was 45 mm.

The fiber used to compose the second fiber layer was a mixture of a concentric core-sheath composite fiber B having polyethylene terephthalate as the core component and polyethylene as the sheath component, coated with a non-durable hydrophilic agent (hereunder referred to as "fiber B"), and an eccentric core-sheath composite fiber C having polyethylene terephthalate as the core component and polyethylene as the sheath component, coated with a durable hydrophilic agent (hereunder referred to as "fiber C") (mass ratio: 1:1). The mean size of the concentric core-sheath composite fiber B was 3.3 dtex, and the mean fiber length was 38 mm. The mean size of the eccentric core-sheath composite fiber C was 2.2 dtex, and the mean fiber length was 44 mm.

A web was produced as a layered body of a first fiber layer (basis weight: 20 g/m$^2$) and a second fiber layer (basis weight: 10 g/m$^2$), using a carding machine at a speed of 20 m/min. Gas spray treatment was carried out on the surface of the first fiber layer.

(2) Production of Nonwoven Fabric

The web produced in (1) above and the nonwoven fabric production apparatus 300 shown in FIG. 12 were used to produce a nonwoven fabric having a skin side surface with a ridge-furrow structure formed therein.

The settings for the nonwoven fabric production apparatus 300 were as follows.
Diameter of spray opening 332: 1.0 mm (circular)
Pitch of spray opening 322: 3.0 mm
Spray gas temperature: 310° C.
Spray gas airflow rate per spray opening: 5 L/min Web transport speed: 100 m/min
Air-permeable supporting member 310 (net-like supporting member): 70 mesh
Heat treatment with heater unit 340: Treatment for 6 seconds with a heat treatment temperature of 140° C., and a through-wind speed of 1.2 m/sec.

Comparative Example 1

(1) Production of Web

A web was produced as a layered body of a first fiber layer and a second fiber layer.

The fiber used to compose the first fiber layer was a mixture of a concentric core-sheath composite fiber D having polyethylene terephthalate as the core component and polyethylene as the sheath component, coated with a durable hydrophilic agent (hereunder referred to as "fiber D), and an eccentric core-sheath composite fiber E having polyethylene terephthalate as the core component and polyethylene as the sheath component, coated with a durable hydrophilic agent (hereunder referred to as "fiber E") (mass ratio: 1:1). The mean size of the concentric core-sheath composite fiber D was 2.2 dtex, and the mean fiber length was 45 mm. The mean size of the eccentric core-sheath composite fiber E was 2.2 dtex, and the mean fiber length was 44 mm.

The fiber used to compose the second fiber layer was a concentric core-sheath composite fiber F having polyethylene terephthalate as the core component and polyethylene as the sheath component, coated with a non-durable hydrophilic agent (hereunder referred to as "fiber F"). The mean size of the concentric core-sheath composite fiber F was 2.8 dtex, and the mean fiber length was 44 mm.

A web was produced as a layered body of a first fiber layer (basis weight: 10 g/m$^2$) and a second fiber layer (basis weight: 20 g/m$^2$), using a carding machine at a speed of 20 m/min.

(2) Production of Nonwoven Fabric

A nonwoven fabric was produced using the web produced in (1) above, in the same manner as Example 1 except that gas spray treatment with the sprayer 330 was not carried out.

Test Example 1

The dry thicknesses and wet thicknesses of the nonwoven fabrics produced in Example 1 and Comparative Example 1 were measured.

The method for measuring the dry thickness and wet thickness of each nonwoven fabric was as follows.

The dry thickness of the nonwoven fabric produced in Example 1 was 0.86 mm, and the wet thickness was 0.79 mm. The wet thickness corresponded to 91% of the dry thickness.

The dry thickness of the nonwoven fabric produced in Comparative Example 1 was 0.78 mm, and the wet thickness was 0.62 mm. The wet thickness corresponded to 80% of the dry thickness.

[Test Example 2] Measurement of Urine Absorption Time

The urine absorption time was measured using a commercially available urine-absorbing pad without a ridge-furrow structure formed on the skin side surface of the top sheet (comparison product), and a urine-absorbing pad having the same construction as the comparison product except for using the nonwoven fabric produced in Example 1 as the top sheet (invention product). The urine samples used were urine samples A, B and C, taken from bedridden elderly individuals A, B and C.

A cylinder with a 60 mm diameter was placed on the urine-absorbing pad, and 80 mL of the urine sample was injected into the cylinder at an injection rate of 10 mL/sec. The time after the start of injection until the urine residing in the cylinder disappeared was measured, and was recorded as the 1st urine absorption time (sec).

At 5 minutes after the start of injection of the first urine sample, a load of 200 g was applied to the cylinder and 80 mL of urine sample was injected at an injection rate of 10 mL/sec (2nd time). The time after the start of the second injection until the urine residing in the cylinder disappeared was measured, and was recorded as the 2nd urine absorption time (sec).

At 10 minutes after the start of injection of the first urine sample, a load of 200 g was applied to the cylinder and 80 mL of urine sample was injected at an injection rate of 10 mL/sec (3rd time). The time after the start of third injection until the urine residing in the cylinder disappeared was measured, and was recorded as the 3rd urine absorption time (sec).

When the comparison product was used, the first, second and third absorption times for general adult urine were 10 seconds, 16 seconds and 23 seconds, respectively, whereas the first, second and third absorption times for urine sample A were 10 seconds, 31 seconds and 72 seconds, respectively, the first, second and third absorption times for urine sample B were 10 seconds, 34 seconds and 125 seconds, respectively, and the first, second and third absorption times for urine sample C were 15 seconds, 57 seconds and 153 seconds, respectively. When urine was repeatedly absorbed with the comparison product, the urine absorption time increased notably. When the surface of the top sheet of the comparison product was observed with a microscope, solid components (cell fragments, crystals and the like) were observed in the urine. The urine of bedridden elderly contains more solid components than general adult urine, and residue of the solid components in the top sheet can result in reduced liquid permeability of the top sheet.

In contrast, when the invention product was used, the first, second and third absorption times for urine sample A were 8 seconds, 17 seconds and 26 seconds, whereas the first, second and third absorption times for urine sample B were 9 seconds, 20 seconds and 40 seconds, respectively, and the first, second and third absorption times for urine sample C were 10 seconds, 32 seconds and 59 seconds, respectively. The urine absorption time was notably reduced compared to the comparison product.

Example 2

(1) Production of Web

Web No. 2-1 was produced as a layered body of a first fiber layer and a second fiber layer.

The fiber used to compose the first fiber layer was composite fiber K having polyethylene terephthalate as the core component and polyethylene as the sheath component, coated with a durable hydrophilic agent (hereunder referred to as "fiber K"). The mean size of composite fiber K was 2.2 dtex, and the mean fiber length was 45 mm.

The fiber used to compose the second fiber layer was a mixture of fiber K with composite fiber L having polyethylene terephthalate as the core component and polyethylene as the sheath component, coated with a non-durable hydrophilic agent (hereunder referred to as "fiber L") (mass ratio 1:1). The mean size of composite fiber L was 2.2 dtex, and the mean fiber length was 50 mm.

A web was produced as a layered body of a first fiber layer (basis weight: 17.5 g/m$^2$) and a second fiber layer (basis weight: 17.5 g/m$^2$), using a carding machine at a speed of 20 m/min. Gas spray treatment was carried out on the surface of the first fiber layer.

(2) Production of Nonwoven Fabric

Using the same nonwoven fabric production apparatus 300 as Example 1, nonwoven fabric No. 2-1 having a ridge-furrow structure formed in the skin side surface was produced from web No. 2-1. The properties of nonwoven fabric No. 2-1 are shown in Table 1.

Comparative Example 2

Nonwoven fabric No. 2-2 was prepared in the same manner as Example 2, except that the fiber used to compose the second fiber layer was fiber L alone. The properties of nonwoven fabric No. 2-2 are shown in Table 1.

Comparative Example 3

Nonwoven fabric No. 2-3 was prepared in the same manner as Example 2, except that fiber used to compose the second fiber layer was composite fiber K coated with a durable hydrophilic agent having lower durability than the durable hydrophilic agent coated onto fiber K (hereunder, "fiber M"). The mean size of composite fiber M was 2.2 dtex, and the mean fiber length was 45 mm. The properties of nonwoven fabric No. 2-3 are shown in Table 1.

Comparative Example 4

Nonwoven fabric No. 2-4 was prepared in the same manner as Example 2, except that the fiber used to compose the first fiber layer was composite fiber N having polyethylene terephthalate as the core component and polyethylene as the sheath component, coated with a durable hydrophilic agent (hereunder referred to as "fiber N"), and the fiber used to compose the second fiber layer was fiber K alone. The mean size of composite fiber N was 1.3 dtex, and the mean fiber length was 40 mm. The properties of nonwoven fabric No. 2-4 are shown in Table 1.

Comparative Example 5

Nonwoven fabric No. 2-5 was prepared in the same manner as Example 2, except that the fiber used to compose the second fiber layer was a mixture of fiber K with composite fiber O having polyethylene terephthalate as the core component and polyethylene as the sheath component, coated with a water-repellent agent (hereunder referred to as "fiber O") (mass ratio 1:1). The mean size of composite fiber O was 2.2 dtex, and the mean fiber length was 45 mm. The properties of nonwoven fabric No. 2-5 are shown in Table 1.

Fiber O is assumed to be fiber that is not coated with a hydrophilic agent.

Comparative Example 6

Nonwoven fabric No. 2-6 having a flat skin side surface was prepared in the same manner as Example 2, except that gas spray treatment with the sprayer 330 was not carried out. The properties of nonwoven fabric No. 2-6 are shown in Table 1.

Comparative Example 7

Nonwoven fabric No. 2-7 having a flat skin side surface was prepared in the same manner as Comparative Example 2, except that gas spray treatment with the sprayer 330 was not carried out. The properties of nonwoven fabric No. 2-7 are shown in Table 1.

TABLE 1

| | | Example No. | | | | | | |
|---|---|---|---|---|---|---|---|---|
| | | Example 2 | Comparative Example 2 | Comparative Example 3 | Comparative Example 4 | Comparative Example 5 | Comparative Example 6 | Comparative Example 7 |
| Nonwoven fabric | No. | No. 2-1 | No. 2-2 | No. 2-3 | No. 2-4 | No. 2-5 | No. 2-6 | No. 2-7 |
| | Basis weight (g/m$^2$) | 35 | 35 | 35 | 35 | 35 | 35 | 35 |
| | Skin side surface | Ridge-furrow | Ridge-furrow | Ridge-furrow | Ridge-furrow | Ridge-furrow | Flat | Flat |
| First fiber layer | Basis weight (g/m$^2$) | 17.5 | 17.5 | 17.5 | 17.5 | 17.5 | 17.5 | 17.5 |
| | Fiber | Fiber K | Fiber K | Fiber K | Fiber N | Fiber K | Fiber K | Fiber K |
| | Hydrophilic agent | Durable | Durable | Durable (high) | Durable | Durable | Durable | Durable |

TABLE 1-continued

| | | Example 2 | Comparative Example 2 | Comparative Example 3 | Comparative Example 4 | Comparative Example 5 | Comparative Example 6 | Comparative Example 7 |
|---|---|---|---|---|---|---|---|---|
| Second fiber layer | Basis weight (g/m$^2$) | 17.5 | 17.5 | 17.5 | 17.5 | 17.5 | 17.5 | 17.5 |
| | Fiber | Fiber K/Fiber L | Fiber L | Fiber M | Fiber K | Fiber K/Fiber O | Fiber K/Fiber L | Fiber L |
| | Hydrophilic agent | Durable/Initial | Initial | Durable (low) | Durable | Durable/water repellent | Durable/Initial | Initial |
| 1st time | TS migration time (sec) | 19.0 | 18.8 | 18.9 | 18.0 | 18.6 | 19.7 | 20.4 |
| | Absorbent body migration time (sec) | 3.8 | 3.3 | 5.7 | 8.2 | 4.4 | 7.2 | 5.0 |
| 2nd time | TS migration time (sec) | 23.6 | 24.0 | 25.8 | 24.5 | 26.3 | 32.2 | 34.3 |
| | Absorbent body migration time (sec) | 12.1 | 12.2 | 12.7 | 24.7 | 14.8 | 15.0 | 14.2 |
| 3rd time | TS migration time (sec) | 27.1 | 28.7 | 31.4 | 29.3 | 34.9 | 48.5 | 57.2 |
| | Absorbent body migration time (sec) | 29.3 | 41.0 | 30.8 | 65.0 | 45.3 | 38.0 | 40.2 |
| | Measurement variation | G | P | P | P | P | G | P |
| | TS void amount | G | VG | F | P | P | P | P |
| | Flow passage of urine through absorbent body surface | G | P | G | VG | VG | VG | VG |

Test Example 3

The top sheet was released from a commercially available urine-absorbing pad, and one of nonwoven fabric Nos. 2-1 to 2-7 cut to the same size was situated in place of the released top sheet, to prepare urine-absorbing pad Nos. 2-1 to 2-7.

Artificial urine was prepared by dissolving 200 g of urea, 80 g of sodium chloride, 8 g of magnesium sulfate, 3 g of calcium chloride and approximately 1 g of dye (Blue #1) in 10 L of ion-exchanged water. Next, artificial elderly urine was prepared by mixing hydrophilic particles, as solid components in urine, with the artificial urine.

An acrylic board mounting a cylinder with an inner diameter of 30 mm (the acrylic board having a hole with an inner diameter of 30 mm, and mounted so that the hole of the acrylic board matched the bottom side of the cylinder) was placed on each of urine-absorbing pad Nos. 2-1 to 2-7, a 2 kg load was applied to the acrylic board, and 150 mL of artificial elderly urine was injected (1st time) into the cylinder at an injection rate of 10 mL/sec. The time after the start of injection until the artificial urine residing in the cylinder reached the top sheet was measured as the "TS migration time (1st time)", and then the time from migration of the artificial urine into the top sheet until the artificial urine migrated to the absorbent body was measured as the "absorbent body-migration time (1st time)".

At 5 minutes after the start of injection of the first artificial urine, 150 mL of artificial urine was injected at an injection rate of 10 mL/sec (2nd time). After start of injection of the second artificial urine, the "TS migration time (2nd time)" and "absorbent body-migration time (2nd time)" were measured in the same manner as the 1st time.

At 10 minutes after the start of injection of the first artificial urine, 150 mL of artificial urine was injected at an injection rate of 10 mL/sec (3rd time). After start of injection of the third artificial urine, the "TS migration time (3rd time)" and "absorbent body-migration time (3rd time)" were measured in the same manner as the 1st time.

The experiment was conducted 10 times for each of urine-absorbing pad Nos. 2-1 to 2-7, and the average value for each was used. The results are shown in Table 1.

Also, the variation in measured values between the "TS migration time (3rd time)" and "absorbent body-migration time (3rd time)" for each of urine-absorbing pad Nos. 2-1 to 2-7 was evaluated based on the following criteria. The results are shown in Table 1.

G: All 10 measured values in a range of within ±5% of the average value.

P: Some of the 10 measured values exceeded ±5% of the average value.

Also, after the third dropping of artificial urine for each of urine-absorbing pad Nos. 2-1 to 2-7, the amount of voids (TS void amount) at the dropping location of the artificial urine on the top sheet was evaluated based on the following criteria.

VG: Minimal adhesion of hydrophilic particles on top sheet, voids of top sheet maintained.

G: Adhesion of hydrophilic particles on top sheet, but voids of top sheet maintained.

F: Top sheet collapsed, or hydrophilic particles blocking top sheet, and fewer voids of top sheet.

P: Top sheet collapsed, or hydrophilic particles blocking top sheet, and very few voids of top sheet.

Also, after the third dropping of artificial urine for each of the urine-absorbing pad Nos. 2-1 to 2-7, the top sheet was released and the flow passage of urine on the surface of the absorbent body at the artificial urine dropping location was evaluated based on the following criteria.

VG: Few hydrophilic particles on absorbent body surface, flow passage of urine on absorbent body surface maintained.

G: Hydrophilic particles on absorbent body surface, flow passage of urine on absorbent body surface maintained.

F: Hydrophilic particles on absorbent body surface, reduced flow passage of urine on absorbent body surface.

P: Absorbent body surface covered with hydrophilic particles, very minimal flow passage of urine on absorbent body surface.

When the urine-absorbing pad No. 2-1 of Example 2 is compared with the urine-absorbing pad No. 2-2 of Comparative Example 2, it is seen that the urine-absorbing pad No. 2-2 of Comparative Example 2 had a longer absorbent body-migration time for the third artificial urine dropping. This is presumably because during the third artificial urine dropping, there was little non-durable hydrophilic agent in the second fiber layer and the hydrophobicity of the second fiber layer was increased, impeding permeation of the artificial urine through the second fiber layer. In addition, it is believed that as the hydrophobicity of the second fiber layer increased it was more difficult for hydrophilic particles to adhere to the fibers in the second fiber layer, and the hydrophilic particles were present on the surface of the absorbent body, inhibiting migration of the artificial urine into the absorbent body. Furthermore, in the urine-absorbing pad No. 2-2 of Comparative Example 2, some of the 10 measured values indicated time required for absorption that deviated by +30% from the average, and therefore repeated absorption of urine by the urine-absorbing pad could potentially result in leakage of urine during actual use.

When the urine-absorbing pad No. 2-1 of Example 2 and the urine-absorbing pad No. 2-3 of Comparative Example 3 are compared, the urine-absorbing pad No. 2-3 of Comparative Example 3 had a slower absorbent body-migration time, and with the urine-absorbing pad No. 2-3 of Comparative Example 3, some of the 10 measured values indicated times required for absorption that deviated by +20% from the average, and therefore repeated absorption of urine by the urine-absorbing pad could potentially result in leakage of urine during actual use. Moreover, while this may be attributed to the high hydrophilicity of the top sheet, locations were confirmed in the top sheet in which numerous hydrophilic particles were adhering and few voids were present.

When the urine-absorbing pad No. 2-1 of Example 2 and the urine-absorbing pad No. 2-4 of Comparative Example 4 are compared, the urine-absorbing pad No. 2-4 of Comparative Example 4 had a longer absorbent body-migration time for all of the first to third artificial urines. This suggests that while artificial urine that has reached the surface of the top sheet migrates relatively smoothly into the first fiber layer, the first fiber layer and second fiber layer retain the artificial urine, thereby slowing migration into the absorbent body. Furthermore, since the first fiber layer and second fiber layer are hydrophilic, the hydrophilic particles adhere in the top sheet, reducing the amount of voids in the top sheet.

When the urine-absorbing pad No. 2-1 of Example 2 and the urine-absorbing pad No. 2-5 of Comparative Example 5 are compared, the urine-absorbing pad No. 2-5 of Comparative Example 5 had a longer TS migration time and absorbent body-migration time from the second artificial urine dropping onward. This is presumably because in the urine-absorbing pad No. 2-5 of Comparative Example 5, fibers coated with a water-repellent agent, assumed to be fibers not coated with a hydrophilic agent, were present in the second fiber layer, and therefore the absorbed artificial urine was impeded from spreading in the planar direction (in the direction of higher hydrophilicity), resulting in adhesion of hydrophilic particles and reduction in permeation of the artificial urine through the top sheet.

When the urine-absorbing pad No. 2-1 of Example 2 and the urine-absorbing pad Nos. 2-6 and 2-7 of Comparative Examples 6 and 7 are compared, the urine-absorbing pad Nos. 2-6 and 2-7 of Comparative Examples 6 to 8 which had flat skin side surfaces all had inferior absorption for artificial urine, while the top sheets collapsed, a large amount of hydrophilic particle adhesion occurred, and the amount of voids in the top sheet was extremely low.

REFERENCE SIGNS LIST

100 Urine-absorbing pad
200 Exterior body
111, 211 Abdomen side section
112, 212 Crotch section
113, 213 Back side section
120, 220 Liquid-permeable top sheet
121, 220 Top sheet skin side surface
122 Ridge (example of projection)
123 Furrow (example of recess)
124 Ridge-furrow structure (example of irregular structure)
130, 230 Liquid-impermeable back sheet
140, 240 Absorbent body
140a First absorbing layer
140b Second absorbing layer
141 Through-hole
141a (First absorbing layer) through-hole
141b (Second absorbing layer) through-hole
142, 143 Compressed section
160 Fluid-absorbing sheet
163 Absorbent polymer layer
250a, 250b Side sheet
255a, 255b Leakproof section

The invention claimed is:

1. An absorbent article for absorbing urine containing a solid component,
   wherein the absorbent article comprises a liquid-permeable top sheet, a liquid-impermeable back sheet and a liquid-absorbing absorbent body disposed between the top sheet and the back sheet, and has a lengthwise direction, a widthwise direction and a thickness direction that are mutually orthogonal,
   the top sheet is a nonwoven fabric with a skin side surface in which a projection is formed,
   a content of fibers oriented in the thickness direction at the projection of the nonwoven fabric is greater than a content of fibers oriented in the thickness direction at a section other than the projection of the nonwoven fabric,
   a wet thickness of the nonwoven fabric is at least 85% of a dry thickness of the nonwoven fabric, and
   the nonwoven fabric has a first fiber layer with a skin side surface and a second fiber layer located more toward the absorbent body side than the first fiber layer, the first fiber layer is composed of fibers with durable hydrophilicity and the second fiber layer is composed of fibers with durable hydrophilicity and fibers with non-durable hydrophilicity.

2. The absorbent article according to claim 1, wherein the dry thickness of the nonwoven fabric is 0.6 to 1.6 mm.

3. The absorbent article according to claim 1, wherein a basis weight of the nonwoven fabric is 18 to 40 g/m$^2$.

4. The absorbent article according to claim 1, wherein the nonwoven fabric is produced by spraying gas onto a web containing thermoplastic resin fibers to form a web having an irregular structure, and then heating the web having the irregular structure to cause heat fusion of crossing sections of the thermoplastic resin fibers therein.

5. The absorbent article according to claim 1, wherein the absorbent body has a through-hole running through the absorbent body in the thickness direction or a recess that opens to the top sheet side, the through-hole or recess extends in the lengthwise direction, through a center in the widthwise direction of the absorbent body.

6. The absorbent article according to claim 5, wherein the absorbent body has a compressed section formed by compressing the absorbent body in the thickness direction, further on an outer side in the widthwise direction than the through-hole or recess.

7. The absorbent article according to claim 5, wherein a fluid-absorbing sheet is disposed between the top sheet and the absorbent body, the fluid-absorbing sheet has two liquid-permeable sheets and an absorbent polymer layer disposed between the two liquid-permeable sheets, while the fluid-absorbing sheet is disposed so that the fluid-absorbing sheet does not overlap the through-hole or recess in the thickness direction.

8. The absorbent article according to claim 1, wherein the projection is a plurality of ridges extending in the lengthwise direction, and furrows are formed between the plurality of ridges, extending in the lengthwise direction.

9. A wearable article, comprising:
an absorbent article; and
an exterior body, provided with a liquid-permeable top sheet with a fitting side in which the absorbent article is fitted, and a liquid-impermeable back sheet, and having an abdomen side section, a crotch section and a back side section,
wherein
the absorbent article is fitted in a detachable manner on the fitting side,
the absorbent article is configured to absorb urine containing a solid component,
the absorbent article includes a liquid-permeable top sheet, a liquid-impermeable back sheet and a liquid-absorbing absorbent body disposed between the top sheet of the absorbent article and the back sheet of the absorbent article, and has a lengthwise direction, a widthwise direction and a thickness direction that are mutually orthogonal,
the top sheet of the absorbent article is a nonwoven fabric with a skin side surface in which a projection is formed,
a content of fibers oriented in the thickness direction at the projection of the nonwoven fabric is greater than a content of fibers oriented in the thickness direction at a section other than the projection of the nonwoven fabric,
a wet thickness of the nonwoven fabric is at least 85% of a dry thickness of the nonwoven fabric, and
the nonwoven fabric has a first fiber layer with a skin side surface and a second fiber layer located more toward the absorbent body side than the first fiber layer, the first fiber layer is composed of fibers with durable hydrophilicity and the second fiber layer is composed of fibers with durable hydrophilicity and fibers with non-durable hydrophilicity.

10. A nonwoven fabric for a liquid-permeable top sheet of an absorbent article for absorbing urine containing a solid component, wherein the absorbent article comprises the liquid-permeable top sheet, a liquid-impermeable back sheet and a liquid-absorbing absorbent body disposed between the top sheet and the back sheet, and has a lengthwise direction, a widthwise direction and a thickness direction that are mutually orthogonal,
wherein the nonwoven fabric has a skin side surface in which a projection is formed,
a content of fibers oriented in the thickness direction at the projection of the nonwoven fabric is greater than a content of fibers oriented in the thickness direction at a section other than the projection of the nonwoven fabric,
a wet thickness of the nonwoven fabric is at least 85% of a dry thickness of the nonwoven fabric, and
the nonwoven fabric has a first fiber layer with a skin side surface and a second fiber layer located more toward the absorbent body side than the first fiber layer, the first fiber layer is composed of fibers with durable hydrophilicity and the second fiber layer is composed of fibers with durable hydrophilicity and fibers with non-durable hydrophilicity.

* * * * *